United States Patent [19]

Williams et al.

[11] Patent Number: 5,459,270
[45] Date of Patent: Oct. 17, 1995

[54] AZACYCLIC COMPOUNDS, PROCESSES FOR THEIR PREPARATION AND PHARMACEUTICAL COMPOSITIONS CONTAINING THEM

[75] Inventors: Brian Williams, Great Dunmow; Raymond Baker, Much Hadham; Timothy Harrison, Great Dunmow; Christopher J. Swain, Duxford, all of United Kingdom

[73] Assignee: Merck Sharp & Dohme Limited, Hoddesdon, United Kingdom

[21] Appl. No.: 196,269

[22] PCT Filed: Aug. 13, 1992

[86] PCT No.: PCT/GB92/01503

§ 371 Date: Feb. 16, 1994

§ 102(e) Date: Feb. 16, 1994

[87] PCT Pub. No.: WO93/04040

PCT Pub. Date: Mar. 4, 1993

[30] Foreign Application Priority Data

Aug. 20, 1991 [GB] United Kingdom .................. 9117934
Dec. 2, 1991 [GB] United Kingdom .................. 9125619
Feb. 26, 1992 [GB] United Kingdom .................. 9204119

[51] Int. Cl.[6] ............... C07D 207/12; C07D 211/42; C07D 705/04; C07D 409/04

[52] U.S. Cl. .............. 546/152; 546/174; 546/175; 546/176; 546/180; 546/195; 546/200; 546/209; 546/210; 546/212; 546/213; 546/216; 546/219; 546/220; 546/221; 546/281; 548/146

[58] Field of Search ............... 546/195, 200, 546/216, 209, 210, 212, 213, 219, 220, 221, 281, 152, 174, 175, 176, 180; 548/146

[56] References Cited

FOREIGN PATENT DOCUMENTS

| 0035743 | 3/1981 | European Pat. Off. . |
| 0436334A2 | 12/1990 | European Pat. Off. . |
| 2365391 | 4/1973 | Germany . |
| 90/05729 | 5/1990 | WIPO . |

OTHER PUBLICATIONS

The Journal of Organic Chemistry, vol. 56, No. 18, Aug. 30, 1991, 5237–5239.
I. Ojima et al. J. Org. Chem. 1991, 56, 5263–5277.
Chemical Abstracts, vol. 96, 1982, 607–608.
Chemical Abstracts, vol. 112, 1990 p. 599.
Chemical Abstracts, vol. 95, 1981 p. 677.
J. Am. Chem. Soc., 1983, 105, 6339–6342, M. Yamashita et al.
Chemical Abstracts, vol. 102, 1985, p. 609.
Chemical Abstracts, vol. 102, 1985, 569–570.
J. Am. Chem. Soc., 1983, 105, 6339–6342.

Primary Examiner—C. Warren Ivy
Attorney, Agent, or Firm—J. Eric Thies; David L. Rose

[57] ABSTRACT

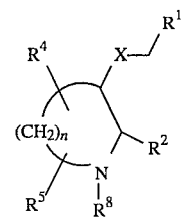

(I)

Compounds of formula (I), and salts and prodrugs thereof wherein n is 1, 2 or 3; X represents O or S; $R^1$ represents optionally substituted phenyl; $R^2$ represents aryl, heteroaryl, benzhydryl, or benzyl; $R^4$ and $R^5$ each independently represent H, halo, $CH_2OR^9$, $C_{1-6}$alkyl, oxo, $CO_2R^{10}$ or $CONR^{10}R^{11}$; $R^8$ represents H, $COR^9$, $CO_2R^{10}$ or optionally substituted $C_{1-6}$alkyl; $R^9$ represents H, $C_{1-6}$alkyl or phenyl; and $R^{10}$ and $R^{11}$ each independently represent H or $C_{1-6}$alkyl; are tachykinin antagonists. They and compositions thereof are useful in medicine.

14 Claims, No Drawings

AZACYCLIC COMPOUNDS, PROCESSES FOR THEIR PREPARATION AND PHARMACEUTICAL COMPOSITIONS CONTAINING THEM

This invention relates to a class of azacyclic compounds, which are useful as tachykinin antagonists. More particularly, the compounds of the invention comprise an azacyclic ring system substituted by an arylmethyloxy or arylmethylthio moiety.

The tachykinins are a group of naturally-occurring peptides found widely distributed throughout mammalian tissues, both within the central nervous system and in the peripheral nervous and circulatory systems. The structures of three known mammalian tachykinins are as follows:
Substance P:
 Arg-Pro-Lys-Pro-Gln-Gln-Phe-Phe-Gly-Leu-Met-$NH_2$
Neurokinin A:
 His-Lys-Thr-Asp-Ser-Phe-Val-Gly-Leu-Met-$NH_2$
Neurokinin B:
 Asp-Met-His-Asp-Phe-Phe-Val-Gly-Leu-Met-$NH_2$ For example, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (December 1987) 8 506–510], specifically in the transmission of pain in migraine (B. E. B. Sandberg et al, J. Med Chem, (1982) 25 1009) and in arthritis [Levine et al in Science (1984) 226 547–549]. These peptides have also been implicated in gastrointestinal (GI) disorders and diseases of the GI tract such as inflammatory bowel disease [Mantyh et al in Neuroscience (1988) 25 (3) 817–37 and D. Regoli in "Trends in Cluster Headache" Ed. Sicuteri et al Elsevier Scientific Publishers, Amsterdam (1987) page 85)]. It is also hypothesised that there is a neurogenic mechanism for arthritis in which substance P may play a role [Kidd et al "A Neurogenic Mechanism for Symmetrical Arthritis" in The Lancet, 11 Nov. 1989 and Grönblad et al "Neuropeptides in Synovium of Patients with Rheumatoid Arthritis and Osteoarthritis" in J. Rheumatol. (1988) 15(12) 1807–10]. Therefore, substance P is believed to be involved in the inflammatory response in diseases such as rheumatoid arthritis and osteoarthritis [O'Byrne et al in Arthritis and Rheumatism (1990) 33 1023–8]. Other disease areas where tachykinin antagonists are believed to be useful are allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9] vasodilation, bronchospasm, reflex or neuronal control of the viscera [Mantyh et al, PNAS (1988) 85 3235–9] and, possibly by arresting or slowing β-amyloid-mediated neurodegenerative changes [Yankner et al Science, (1990) 250, 279–82] in senile dementia of the Alzheimer type, Alzheimer's disease and Down's Syndrome.

Substance P may also play a role in demyelinating diseases such as multiple sclerosis and amyotrophic lateral sclerosis [J. Luber-Narod et. al., poster to be presented at C.I.N.P. XVIIIth Congress, 28th Jun.–2nd Jul., 1992, in press], and in disorders of bladder function such as bladder detrusor hyper-reflexia (Lancet, 16th May, 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythromatosis (European patent application no. 0 436 334), opthalmic disease such as conjuctivitis, vernal conjunctivitis, and the like, and cutaneous diseases such as contact dermatitis, atropic dermatitis, urticaria, and other eczematoid dermatitis (European patent application no. 0 394 989).

In view of their metabolic instability, peptide derivatives are likely to be of limited utility as therapeutic agents. It is for this reason that non-peptide tachykinin antagonists are sought.

European patent application no. 0 436 334 discloses 4-to 7-membered azacyclic compounds substituted at the 3-position by a substituted amino moiety. The compounds are said to be tachykinin antagonists.

The present invention provides a compound of formula (I), or a salt or prodrug thereof:

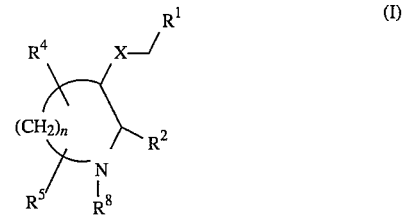

wherein
n is 1, 2 or 3 and where any carbon atom of $(CH_2)_n$ may be substituted by $R^4$ and/or $R^5$;

X represents O or S;

$R^1$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl —$OR^a$, $SR^a$, $SOR^a$, $SO_2R^aR^b$, —$NR^aCOR^b$, —$NR^aCO_2R^b$, —$CO_2R^a$ or —$CONR^aR^b$;

$R^2$ represents aryl selected from phenyl and naphthyl; heteroaryl selected from indazolyl, thienyl, furyl, pyridyl, thiazolyl, tetrazolyl and quinolyl: benzhydryl; or benzyl; wherein each aryl or heteroaryl moiety may be substituted by $C_{1-6}$alkyl, $C_{1-6}$alkoxy, halo or trifluoromethyl;

$R^4$ and $R^5$ each independently represent H, halo, $CH_2OR^9$, $C_{1-6}$alkyl, oxo, $CO_2R^{10}$ or $CONR^{10}R^{11}$;

$R^8$ represents H, $COR^9$, $CO_2R^{10}$, $COCONR^{10}R^{11}$, $COCO_2R^{10}$ or $C_{1-6}$alkyl optionally substituted by a group selected from ($CO_2R^{10}$, $CONR^{10}R^{11}$, hydroxy, cyano $COR^9$, $NR^{10}R^{11}$, $C(NOH)NR^{10}R^{11}$, CONHphenyl($C_{1-4}$alkyl), $COCO_2R^{10}$, $COCONR^{10}R^{11}$ and phenyl optionally substituted by one or more substituents selected from $C_{1-6}$alkyl, $C_{1-6}$alkoxy, halo and trifluoromethyl);

$R^a$ and $R^b$ each independently represent H, $C_{1-6}$alkyl, phenyl or trifluoromethyl;

$R^9$ represents H, $C_{1-6}$alkyl or phenyl; and $R^{10}$ and $R^{11}$ each independently represent H or $C_{1-6}$alkyl.

One subgroup of compounds according to the invention is represented by compounds wherein n is 2 or 3; $R^4$ and $R^5$ each independently represent H, halo, $C_{1-6}$alkyl, $CO_2R^{10}$ or $CONR^{10}R^{11}$; and $R^8$ represents H, $COR^9$ or $C_{1-6}$alkyl optionally substituted by a group selected from ($CO_2R^{10}$, $CONR^{10}R^{11}$ and phenyl optionally substituted by $C_{1-6}$alkyl, $C_{1-6}$alkoxy, halo or trifluoromethyl).

A further subgroup of compounds according to the invention is represented by compounds wherein n is 2 or 3; $R^2$ represents phenyl or benzhydryl wherein any of the phenyl rings of the phenyl or benzhydryl moieties may optionally be substituted by halo or trifluoromethyl; $R^4$ and $R^5$ each independently represent H, $C_{1-6}$alkyl or $CO_2(C_{1-6}$alkyl); and $R^8$ represents H or $C_{1-6}$alkyl.

Preferably n is 2 or 3, more preferably 3.

Preferably X represents O.

Preferably $R^1$ represents substituted phenyl. When $R^1$ is substituted phenyl suitable substituents include $C_{1-6}$alkyl especially $C_{1-4}$alkyl such as methyl and t-butyl, nitro, trifluoromethyl, trimethylsilyl, halo such as bromo, chloro and iodo, carboxy, cyano, $C_{1-6}$alkoxy such as methoxy and amino. Preferably $R^1$ represents phenyl substituted by one or more groups selected from methyl, trifluoromethyl and halo, especially chloro. When monosubstituted, the substituent is suitably in the 3-position of the phenyl ring. More preferably $R^1$ represents disubstituted phenyl. Particularly preferred are compounds of formula (I) wherein $R^1$ represents 3,5-disubstituted phenyl, especially 3,5-bis(trifluoromethyl)phenyl.

Suitable values for the group $R^2$ include aryl such as substituted or unsubstituted phenyl, 5-membered heteroaryl such as thienyl, 6-membered heteroaryl such as pyridyl, and benzhydryl.

Preferably $R^2$ represents unsubstituted or substituted phenyl or thienyl, pyridyl or benzhydryl. When $R^2$ is substituted phenyl, suitable phenyl substituents include $C_{1-6}$alkyl, such as methyl, and halo, such as chloro. Particularly preferred are compounds of formula (I) wherein $R^2$ represents unsubstituted phenyl.

Suitable values for $R^4$ and $R^5$ include H, $C_{1-6}$alkyl, especially methyl, $CH_2OR^9$ such as hydroxymethyl and oxo. The substituents $R^4$ and $R^5$ may be located on any available ring carbon atom, including (except when they represent oxo) C-2 and C-3, but will preferably be located at the 6-position. Preferably at least one of $R^4$ and $R^5$ represents H. In one preferred group of compounds $R^4$ and $R^5$ both represent H. In a further preferred group of compounds one of $R^4$ and $R^5$ is H and the other is 6-hydroxymethyl.

Suitable values for $R^8$ include H, $COR^9$ such as CHO and $COCH_3$, $CO_2R^{10}$, such as $CO_2C_{1-6}$alkyl e.g. $CO_2C_{1-4}$alkyl such as $CO_2$t-butyl, $COCONR^{10}R^{11}$, such as $COCONH_2$, $COCO_2R^{10}$, such as $COCO_2C_{1-4}$alkyl, for example, $COCO_2CH_3$, $C_{1-6}$alkyl, such as methyl, and substituted $C_{1-6}$alkyl e.g. substituted $C_{1-3}$alkyl such as methyl, ethyl or n-propyl, such as $C_{1-6}$alkyl substituted by $CO_2R^{10}$, especially $CO_2CH_3$ and $CO_2H$, $CONR^{10}R^{11}$ especially $CONH_2$, $CONHCH_3$, CONH(t-butyl), CONH(cyclopropyl) and $CON(CH_2CH_3)_2$, cyano, $C(NOH)NR^{10}R^{11}$, especially $C(NOH)NH_2$, CONHphenyl($C_{1-4}$alkyl), especially CONHbenzyl, and optionally substituted phenyl, especially unsubstituted phenyl and phenyl substituted by one or more of $C_{1-6}$alkoxy, such as methoxy or trifluoromethyl.

In one preferred group of compounds of formula (I), $R^8$ represents H.

In a further preferred group of compounds of formula (I), $R^8$ represents $C_{1-6}$alkyl substituted by $CO_2R^{10}$ or $CONR^{10}R^{11}$, more preferably $R^8$ represents $CH_2CO_2R^{10}$, $CH(CH_3)CO_2R^{10}$, $CH_2CONR^{10}R^{11}$ or $CH(CH_3)CONR^{10}R^{11}$, especially $CH_2CO_2CH_3$, $CH(CH_3)CO_2CH_3$, $CH_2CONH_2$ or $CH(CH_3)CONH_2$.

The alkyl, alkenyl and alkynyl groups referred to with respect to the formulae herein may represent straight, branched or cyclic groups or combinations thereof. Thus, for example, suitable alkyl groups include methyl, ethyl, n- or iso-propyl, n-, sec-, iso- or tert-butyl, cyclopropyl, cyclobutyl, cyclopentyl or cyclohexy, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo.

For use in medicine, the salts of the compounds of formula (I) will be non-toxic pharmaceutically acceptable salts. Other salts may, however, be useful in the preparation of the compounds according to the invention (such as the dibenzoyltartrate salts) or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, oxalic acid, fumaric acid, maleic acid, succinic acid, acetic acid, citric acid, tartaric acid, carbonic acid, phosphoric acid or p-toluenesulphonic acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

Preferred salts of the compounds according to the invention include the hydrochloride, hydrobromide and p-toluenesulphonic acid salts, especially the hydrobromide salt.

The present invention includes within its scope prodrugs of the compounds of formula (I) above. In general, such prodrugs will be functional derivatives of the compounds of formula I which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. It is to be understood that all such isomers and mixtures thereof are encompassed within the scope of the present invention.

A particular sub-class of compounds according to the invention is represented by compounds of formula (Ia), and salts and prodrugs thereof:

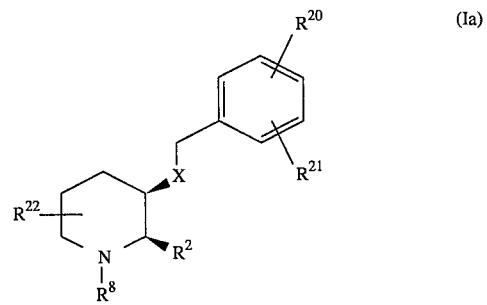

(Ia)

wherein $R^2$, $R^8$ and X are as defined for formula (I);

$R^{20}$ and $R^{21}$ independently represent H, $C_{1-6}$alkyl, $C_{2-6}$alkenyl, $C_{2-6}$alkynyl, halo, cyano, nitro, trifluoromethyl, trimethylsilyl, $OR^a$, $SR^a$ $SOR^a$, $SO_2R^a$, $NR^aR^b$, $NR^aCOR^b$, $NR^aCO_2R^b$, $CO_2R^a$ or $CONR^aR^b$, where $R^a$ and $R^b$ are as previously defined; and $R^{22}$ represents H, $C_{1-6}$alkyl, $CH_2OR^9$ or oxo, preferably H.

Particular values of $R^{20}$ and $R^{21}$ include H, methyl, butyl, halo, trimethylsilyl, trifluoromethyl, nitro, carboxy, cyano and amino. Preferably $R^{20}$ and $R^{21}$ are both other than H and are located at the 3-and 5-positions of the phenyl ring. More preferably $R^{20}$ and $R^{21}$ each represent trifluoromethyl.

$R^{22}$ may be located on any available carbon atom of the piperidine ring. In particular when $R^{22}$ is $C_{1-6}$alkyl or $CH_2OR^9$, it may be located at the 2-, 3-, or 6-position of the piperidine ring, preferably the 6-position. When $R^{22}$ is oxo, it is preferably located at the 6-position.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout .the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The present invention futher provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; neurodegenerative disorders such as dementia, including senile dementia of the Alzheimer type, Alzheimer's disease and Down's syndrome; demyelinating diseases such as MS and ALS and other neuropathological disorders such as peripheral neuropathy, for example, diabetic and chemotherapy-induced neuropathy, and postherpetic and other neuralgias; respiratory diseases such as chronic obstrucutive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine. For example, the compounds of formula (I) may suitably be used in the treatment of disorders of the central nervous system such as anxiety, psychosis and schizophrenia; neurodegenerative disorders such as senile dementia of the Alzheimer type, Alzheimer's disease and Down's syndrome; respiratory diseases such as bronchospasm and asthma; inflammatory diseases such as inflammatory bowel disease, osteoarthritis and rheumatoid arthritis; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; and pain or nociception, for example, that attributable to or associated with any of the foregoing conditions or the transmission of pain in migraine.

The compounds of formula (I) are particularly useful in the treatment of pain or nociception and/or inflammation and disorders associated therewith such as, for example, neuropathy, such as diabetic or peripheral neuropathy and chemotherapy-induced neuropathy, postherpetic and other neuralgias, asthma, osteoarthritis, rheumatoid arthritis and especially migraine.

The present invention further provides a compound of formula (I) for use in therapy. According to a further or alternative aspect, the present invention provides a compound of formula (I) for use in the manufacture of a medicament for the treatment of physiological disorders associated with an excess of tachykinins, especially substance P. The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (I).

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day. For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

The compounds according to the invention may be prepared by a process which comprises reacting a compound of formula (III) with a compound of formula (IV):

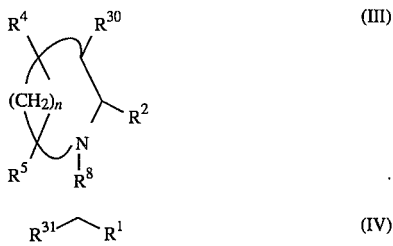

wherein $R^1$, $R^2$, $R^4$, $R^5$ and n are as defined for formula (I), $R^8$ is as defined for formula (I) except that, when $R^8$ is H it is replaced by a suitable protecting group, such as $CO_2(C_{1-6}alkyl)$; and one of $R^{30}$ and $R^{31}$ represents a leaving group and the other of $R^{30}$ and $R^{31}$ represents XH, where X is as defined for formula (I); in the presence of a base, followed by deprotection, if required.

Suitably $R^{30}$ represents XH and $R^{31}$ represents a leaving group.

Suitable leaving groups include halo, e.g. chloro, bromo or iodo, or sulphonate derivatives such as tosylate or mesylate.

The reaction is conveniently carried out in a suitable organic solvent, such as an ether, e.g. 1,2-dimethoxyethane, at a temperature in the region of 0° C. Favoured bases of use in the reaction include alkali metal amides and hydrides, such as potassium bis(trimethylsilyl)amide or potassium hydride. Suitably, potassium bis(trimethylsilyl)amide is used.

Compounds of formula (I) may also be prepared from different compounds of formula (I) by interconversion processes. In particular, interconversion processes may be used to vary the group $R^8$. For example, compounds of formula (I) wherein $R^8$ is other than H may be prepared from the corresponding compounds of formula (I) wherein $R^8$ is H by conventional methods, such as reaction with a compound $R^8$-Hal, where Hal represents halo, in the presence of a base. Suitable reagents and conditions will be readily apparent to those skilled in the art and are illustrated by the accompanying Examples. Suitable bases include organic bases, such as tertiary amines, e.g. triethylamine, and inorganic bases, such as alkali metal carbonates, e.g. sodium carbonate. Compounds of formula (I) wherein $R^8$ is $COR^9$ may also be prepared from compounds of formula (I) wherein $R^8$ is H by, for example, reaction with an appropriate acid anhydride. Compounds of formula (I) wherein $R^8$ is $C_{1-6}$alkyl may be prepared from corresponding compounds of formula (I) wherein $R^8$ is $COR^9$ by reduction using, for example, borane or a borohydride such as sodium cyanoborohydride. Suitable procedures are described in the accompanying examples.

Compounds of formula (I) wherein $R^8$ is $C_{1-6}$ alkyl substituted by $CONR^{10}R^{11}$ may be prepared from corresponding compounds of formula (I) wherein $R^8$ is $C_{1-6}$alkyl substituted by $CO_2R^{10}$ by treatment with ammonia or an amine of formula $NR^{10}R^{11}$.

The intermediates of formula (III) above wherein $R^{30}$ is SH may be prepared from the corresponding intermediates of formula (III) wherein $R^{30}$ represents OH by treating the latter compound with Lawesson's reagent or phosphorus pentasulphide in a suitable solvent, e.g. pyridine, at ambient or elevated temperatures, suitably at reflux temperature.

Intermediates of formula (III) above wherein $R^{30}$ is OH may be prepared from corresponding compounds of formula (V):

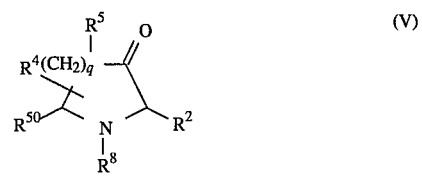

wherein $R^2$, $R^4$, $R^5$ and $R^8$ are as defined for formula III above, q is 1 or 2 and $R^{50}$ is an optional carbonyl group, by reduction. Suitable reducing agents will be readily apparent to one skilled in the art and include, for example, metallic hydrides, such as lithium aluminium hydride or, preferably, sodium borohydride.

Intermediates of formula (III) wherein $R^{30}$ is a leaving group may be prepared from compounds of formula (III) wherein $R^{30}$ is OH, for example, by reaction with a thionyl halide, a mesyl halide or a tosyl halide.

Where they are not commercially available, the intermediates of formula (IV) above may be prepared by the procedures described in the accompanying Examples or by alternative procedures which will be readily apparent to one skilled in the art.

Compounds of formula (V) wherein q is 1, the carbonyl group $R^{50}$ is absent, and $R^5$ represents $CO_2(C_{1-6}alkyl)$, may be prepared by reaction of compounds of formula (VI) with compounds of formula (VII):

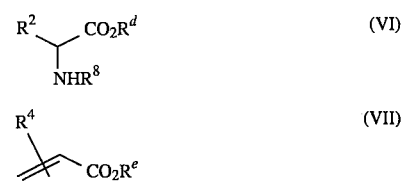

wherein $R^2$ is as above defined, $R^d$ represents $C_{1-6}$alkyl and $CO_2R^e$ is $R^5$; in the presence of a base.

Suitable bases include alkali metal hydrides, such as sodium hydride, and alkali metal alkoxides, such as sodium butoxide. The reaction is conveniently effected in a suitable organic solvent, such as a hydrocarbon, for example, benzene or toluene, or an ether, for example tetrahydrofuran.

Compounds of formula (V) wherein $R^{50}$ is absent and $R^5$ represents $CO_2(C_{1-6}alkyl)$ (VB), may be prepared by reaction of a compound of formula (VI) with a compound of formula (VIIA)

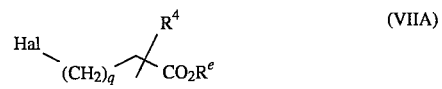

wherein q is 1 or 2 and Hal represents halo, such as chloro, bromo or iodo, and $CO_2R^e$ is as above defined, in the presence of a base, as above described.

Further procedures for the preparation of compounds of formula (V) using the Dieckmann reaction will be apparent to those skilled in the art and are described in the accompanying examples.

Compounds of formula (V) wherein $R^5$ is other than $CO_2(C_{1-6}alkyl)$ may be prepared from compounds of formula (V) wherein $R^5$ represents $CO_2(C_{1-6}alkyl)$ by decarboxylation using, for example, oxalic acid.

Alternatively, compounds of formula (V) wherein q is 2 may be prepared from enamines of formula (VIII):

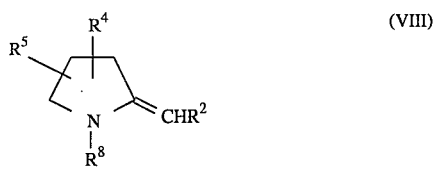

according to the method of Cervinka et al, Collect. Czech. Chem. Commun., 1988, 53, 308–10.

Compounds of formula (V) wherein q is 2 and the carbonyl group $R^{50}$ is present may be prepared from intermediates of formula (IX):

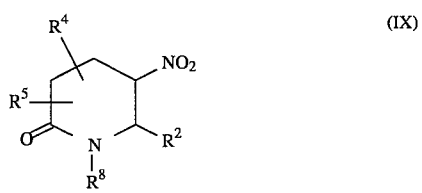

by ozonolysis, or by means of the Nef reaction. Suitable reagents and conditions are described in Organic Reactions, 38, 655.

Compounds of formula (V) wherein one or both of $R^4$ and $R^5$ represents halo, $C_{1-6}$alkyl, $CONR^{10R11}$ or $CO_2R^{10}$ may be prepared from appropriately substituted analogues of the compounds of formulae (VI), (VII) and (VIIA), or by appropriate interconversion procedures which will be readily apparent to those skilled in the art.

Intermediates of formula (VI) wherein $R^d$ is $C_{1-6}$alkyl (VIA) may be prepared from the corresponding compounds of formula (VI) wherein $R^d$ is hydrogen (VIB), by conventional methods.

Intermediates of formula (VIB) may be prepared from the compound of formula (X):

by reaction with a compound $R^2$-Hal, wherein $R^2$ is as above defined and Hal is halo, such as bromo, chloro or iodo, in the presence of a base, followed by hydrolysis and suitable modification of the nitrogen substituent using conventional methods.

Suitable bases of use in the reaction include metal hydroxides, for example, sodium hydroxide. The reaction is conveniently effected in a mixture of water and a suitable organic solvent, such as a hydrocarbon, for example, toluene, in the presence of a phase transfer catalyst, such as benzyltrimethylammonium chloride.

Hydrolysis is conveniently effected by heating a solution of the product of reaction between the compound of formula (IX) and $R^2$-Hal in concentrated hydrochloric acid, at reflux.

The compound of formula (X) is commercially available.

Intermediates of formula (IX) are prepared as described in European Patent Application No. 0 436 334.

Compounds of formula $R^2$-Hal may be prepared according to the procedure described by E. J. Corey, Tetrahedron Lett., 1972, 4339.

Intermediates of formula (III) wherein n is 1 or 2 are novel compounds and constitute a further aspect of the present invention.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. For example, intermediate alcohols of formula (III), wherein $R^{30}$ is OH, may be resolved into their component enantiomers by standard techniques, such as the formation of diastereomeric esters or amides, followed by chromatographic separation or separation by fractional crystallization and removal of the chiral auxiliary. The diastereomeric alcohols can then be used to prepare optically pure compounds of formula (I).

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

The following Examples illustrate the preparation of compounds according to the invention. "Celite" and "Hiflo" are trade marks. THF means tetrahydrofuran. Boc means t-butoxycarbonyl.

EXAMPLE 1: cis 2-(Diphenylmethyl)-3-(3,5-dimethylbenzyloxy)-1-methylpyrrolidine a) Through a solution of 2-amino-3,3-diphenylpropanoic acid hydrochloride (35.0 g, 126 mmol) in methanol (500 ml) was bubbled hydrogen chloride for 3 h. The solution was stirred at room temperature for 120 h and the solvent removed in vacuo. Addition of diethyl ether gave methyl 2-amino-3,3-diphenylpropanoate hydrochloride, m.p.= 213°–215° C.(dec.). $^1$H NMR (360 MHz, DMSO-$d_6$) δ8.70 (3H, vbs), 7.20–7.57 (10H, m), 4.94 (1H, d, J=11 Hz), 4.36 (1H, d, J=11 Hz), 3.39 (3H, s). m/z (CI$^+$) 256(MH).

b) To a solution of methyl 2-amino-3,3-diphenylpropanoate hydrochloride (Example 1a, 28.0 g, 96 mmol), chloroform (250 ml), and 1.0M sodium carbonate (250 ml) was added ethyl chloroformate (9.20 ml, 96 mmol). After the solution had been stirred for 18 h the organic phase was separated, washed with 10% citric acid, water, saturated brine and dried (MgSO$_4$). After removal of the solvent in vacuo the residue was recrystallised from hot methanol to give methyl 2-ethoxycarbonylamino- 3,3-diphenylpropanoate, m.p.=107°–109° C. $^1$H NMR (250 MHz, CDCl$_3$) δ7.18–7.33 (10H, m), 5.12 (1H, br t, J=8.5 Hz), 4.95 (1H, br d, J=8.5 Hz), 4.40 (1H, d, J=8.0 Hz), 4.06 (2H, q, J=7.0 Hz), 3.50 (3H, s), 1.17 (3H, t, J=7.0 Hz). m/z (CI$^+$) 328(MH).

c) To a suspension of 80% sodium hydride (2.48 g, 83 mmol) in benzene (50 ml) was slowly added a solution of methyl 2-ethoxycarbonylamino-3,3-diphenylpropanoate (Example 1b, 27.0 g, 83 mmol) in benzene (200 ml) and the mixture then heated at reflux for 1 h. Ethanol (1.0 ml) followed by ethyl acrylate (8.95 ml, 83 mmol) were added and the reaction heated at reflux for 2 h, the solvent was then distilled off and the residue allowed to cool to room temperature. A solution of the residue in water was added to a concentrated sulphuric acid/ice mixture and the product extracted into ethyl acetate. The organic phase was washed with saturated brine and dried (MgSO$_4$). The residue was chromatographed on silica gel in dichloromethane/methanol (97:3) to give 1,4-bis(ethoxycarbonyl)-2-(diphenylmethyl)-pyrrolidin-3-one, m/z (CI$^+$) 396(MH). A solution of this oil in 1.0M oxalic acid was heated at reflux for 8 h, cooled and the product extracted into chloroform. After separation the chloroform was removed in vacuo and the residue chromatographed on silica gel using ethyl acetate/hexane (1:4) as eluant to give 2-(diphenylmethyl)-1-ethoxycarbonylpyrrolidin-3-one. $^1$H NMR (250 MHz, CDCl$_3$) δ7.14–7.52 (10H, m), 4.80 (1H, br s), 4.68 (1H, vbr s), 4.18 (2H, br q), 3.94 (1H, vbs), 3.06 (1H, m), 2.34 (1H, m), 1.76 (1H, m), 1.22 (3H, t, J=7.0 Hz). m/z (CI$^+$) 324(MH).

d) To a solution of 2-(diphenylmethyl)-1-ethoxycarbonylpyrrolidin-3-one (Example 1c, 5.75 g, 18 mmol) in ethanol (50 ml) was added sodium borohydride (1.00 g, 26 mmol) and the mixture was stirred under nitrogen for 60 h at room temperature. The reaction mixture was partitioned between 10% citric acid/ethyl acetate, the organic phase washed with saturated brine and dried (MgSO$_4$). The solvent was removed in vacuo and the residue chromatographed on silica gel using ethyl acetate/hexane (2:3) as eluant. Recrystallisation from ethyl acetate/hexane gave cis-2-(diphenylmethyl)-3-hydroxy-1-ethoxycarbonylpyrrolidine, m.p.= 104°–105° C. $^1$H NMR (360 MHz, CDCl$_3$) δ7.00–7.50 (10H, m), 4.78 (1H, dd, J=9 Hz and J=7 Hz), 4.46 (1H, dd, J=8.0 Hz and J=7.0 Hz), 4.32 (1H, d, J=9 Hz), 3.83 (2H, m), 3.47 (2H, m), 3.31 (1H, m), 2.10 (1H, m), 1.95 (1H, m), 1.00 (3H, t, J=7.0 Hz).

e) To a solution of cis-2-(diphenylmethyl)-3-hydroxy-1-ethoxycarbonylpyrrolidine (Example 1d, 1.00 g, 3.1 mmol) in ethylene glycol dimethyl ether (10.0 ml) was added 0.5M potassium bis(trimethylsilyl)amide (9.00 ml, 4.5 mmol) and stirred at room temperature for ½h before addition of 3,5dimethylbenzyl bromide (0.92 g, 4.5 mmol) in ethylene glycol dimethyl ether (2 ml). After stirring for 18 h the solvent was removed in vacuo and the residue partitioned between water/dichloromethane. The organic phase was washed with saturated brine and dried (MgSO$_4$). The residue, after removal of solvent in vacuo, was chromatographed on silica gel using ethyl acetate/hexane (2:3) as eluant to give cis-2-(diphenylmethyl)-3-(3,5-dimethylbenzyloxy)-1-ethoxycarbonylpyrrolidine. $^1$H NMR (360 MHz, DMSO-d$_6$) δ7.05–7.46 (10H, m), 6.81 (1H, s), 6.58 (2H, s), 4.86 (1H, t, J=7.0 Hz), 4.42 (1H, d, 7.5 Hz), 4.18 (1H, d, J=12.0 Hz), 4.11 (1H, m), 3.97 (1H, d, J=12.0 Hz), 3.83 (1H, m), 3.68 (1H, m), 3.31 (1H, m), 2.98 (1H, m), 2.19 (6H, s), 2.15 (1H, m), 1.95 (1H, m), 1.03 (3H, t, J=7.0 Hz). m/z (CI$^+$) 444 (MH).

f) To a solution of cis-2-(diphenylmethyl)-3-(3,5-dimethylbenzyloxy)-1-ethoxycarbonylpyrrolidine (Example 1e, 0.500 g, 1.1 mmol) in tetrahydrofuran (5.0 ml) was added 1.0M lithium aluminium hydride (5.0 ml, 5.0 mmol) and then the solution heated at reflux for 1 h. To the cooled solution was carefully added water (2 ml), 4M sodium hydroxide (2 ml) and water (4 ml) followed by ethyl acetate. The suspension was filtered through Celite and the filtrate was washed with saturated brine and dried (MgSO$_4$). Removal of the solvent in vacuo gave cis-2-(diphenylmethyl)-3-(3,5-dimethylbenzyloxy)-1-methylpyrrolidine, as an oil. $^1$H NMR (360 MHz, CDCl$_3$) δ7.05–7.43 (10H, m), 6.85 (1H, s), 6.68 (2H, s), 4.30 (1H, d, J=15.0 Hz), 4.01 (1H, d, J=16.0 Hz), 3.77 (1H, m), 3.63 (1H, d, J=16.0 Hz), 3.24 (2H, m), 2.30 (1H, m), 2.26 (6H, s), 1.91 (5H, m).

EXAMPLE 2:
cis-3-((3,5-Dimethylphenyl)methyloxy)-2-phenylpiperidine hydrochloride salt a) A solution of methyl-4-nitrobutyrate (23 g, 0.156 mol) and benzaldehyde (16 ml, 0.156 mol) in acetic acid (39 ml) containing ammonium acetate (12.12 g, 0.156 mol) was heated at reflux under nitrogen for 2 h. The reaction mixture was cooled to 5° C., whereby a pale-yellow solid crystallised. This was isolated by filtration, then dissolved in dichloromethane, washed cautiously with saturated aqueous sodium bicarbonate solution (2×), then dried (MgSO$_4$) and concentrated to leave a yellow solid. Recrystallisation from ethyl acetate provided 5-nitro-2-oxo-6-phenylpiperidine as a crystalline, white solid. $^1$H NMR (CDCl$_3$) δ7.46–7.26 (m), 6.0 (br s), 5.24 (dd, J=1.4, 7.0 Hz), 4.70 (m), 2.70–2.50 (m), 2.38–2.24 (m).

b) Potassium t-butoxide (1.68 g, 15 mmol) was added to a solution of 5-nitro-2-oxo-6-phenylpiperidine (3 g, 13.6 mmol; Example 2a) in a mixture of dichloromethane (50 ml) and methanol (50 ml) and the mixture was cooled to –78° C. under nitrogen. Ozone was bubbled through the solution for 3 h. A yellow-green solution resulted, and TLC indicated no starting material remained. The reaction mixture was purged with oxygen for 5 min to remove excess ozone, then dimethylsulfide (7 ml) was added and the reaction mixture was allowed to warm to 23° C. The solvent was removed in-vacuo and the residue was partitioned between dichloromethane and water. The layers were separated, and the aqueous phase was extracted twice with dichloromethane. The combined organic extracts were washed with brine, then dried (K$_2$CO$_3$) and concentrated to leave 3,6-diketo-2-phenylpiperidine as a white solid.

This crude material was slurried in dry THF and added to lithium aluminium hydride (1M in THF, 50 ml) then heated at reflux for 12 h. After cooling to 23° C., the reaction mixture was quenched by the cautious addition of water (dropwise) under nitrogen, then 2M sodium hydroxide. The mixture was filtered through a pad of Hiflo, the filtrate was washed with brine, then dried (K$_2$CO$_3$) and concentrated to leave a yellow solid. Purification by silica-gel chromatography (CH$_2$Cl$_2$/MeOH/NH$_3$ 97:3:1 then CH$_2$Cl$_2$/MeOH 95:5) provided 3-hydroxy-2-phenylpiperidine as a mixture of cis- and trans- isomers. $^1$H NMR (CDCl$_3$) 7.44–7.20 (m), 3.84 (s), 3.76 (s), 3.54 (m), 3.4 (s), 3.3 (d, J=8 Hz), 3.26 (m), 3.04 (m), 2.78 (ddd, J=2.9, 11.9, 11.9 Hz), 2.70 (ddd, J=2.9, 11.9, 11.9 Hz), 2.18–1.78 (m), 1.48 (m). MS (EI) m/z 177 (M).

c) Di-t-butyldicarbonate (1.36 g, 6.2 mmol) was added to a solution of 3-hydroxy-2-phenylpiperidine (1 g, 5.6 mmol, Example 2b) in dichloromethane (8 ml) under nitrogen and the mixture stirred at 23° C. for 3 h. The solvent was removed in-vacuo, and the residue purified by silica-gel chromatography (CH$_2$Cl$_2$/MeOH/NH$_3$ 97:3:0.5) to provide cis- and trans-1-t-butyloxycarbonyl-3-hydroxy-2-phenylpiperidine as a clear, viscous oil. $^1$H NMR (CDCl$_3$) δ7.50–7.42 (m), 7.40–7.14 (m), 5.36 (d, J=5.6 Hz), 4.50 (m), 4.44 (m), 4.12–3.92 (m), 3.02 (ddd, J=2.8, 12.6, 12.6 Hz), 2.87 (ddd, J=2.8, 12.6, 12.6 Hz), 1.88–1.66 (m), 1.46 (s), 1.36 (s).

d) To a cooled (0° C.) solution of 1-t-butyloxycarbonyl-3-hydroxy-2-phenylpiperidine (1.4 g, 5.0 mmol, Example 2c) in dry N,N-dimethylformamide (5 ml) was added sodium hydride (80% dispersion in mineral oil; 182 mg, 6.1 mmol). The cooling bath was removed, and the reaction mixture stirred at 23° C. for 0.5 h. A solution of 3,5-dimethylbenzylbromide ( 1.21 g, 6.1 mmol) in dry N,N-dimethylformamide (1 ml) was added, and stirring continued at 23° C. for 17 h. The mixture was diluted with water (100 ml) and extracted with dichloromethane (3×40 ml). The combined organic extracts were washed with brine (1×30 ml) then dried ($K_2CO_3$) and concentrated to leave a pale-yellow oil. Purification by silica gel chromatography (hexanes-ethyl acetate 19:1→9:1→4:1) provided a mixture of cis- and trans- 1-t-butyloxycarbonyl-3-((3,5-dimethylphenyl)methyloxy)-2-phenylpiperidine as a clear, viscous oil. $^1$H NMR ($CDCl_3$) δ7.60 (d, J=8.1 Hz), 7.38–7.14 (m), 7.01 (s), 6.91 (s), 5.71 (br s), 5.60 (br s), 4.67 (app. d, J=11.8 Hz), 4.62 (d, J=11.5 Hz), 4.53 (d, J=11.5 Hz), 4.12 (m), 3.94 (br d, J=13 Hz), 3.82 (m), 2.84 (ddd, J=3.3, 13.1, 13.1 Hz), 2.67 (ddd, J=3.3, 13.1, 13.1 Hz), 2.39 (s), 2.31 (s), 1.99–1.82 (m), 1.69–1.49 (m), 1.51 (s), 1.47 (s).

e) Trifluoroacetic acid (3 ml) was added to 1-t-butyloxycarbonyl-3-((3,5-dimethylphenyl)methyloxy)-2-phenylpiperidine (800 mg Example 2d) under nitrogen and the solution was stirred at 23° C. for 1 h. Excess trifluoroacetic acid was removed in vacuo, and the residue was partitioned between 2M sodium hydroxide and dichloromethane. The layers were separated, and the aqueous phase was extracted twice with dichloromethane. The combined organic phases were dried ($K_2CO_3$) and concentrated to leave a clear, colourless oil. Purification on silica gel ($CH_2Cl_2$/MeOH/$NH_3$ 97:3:0.5 then $CH_2Cl_2$/MeOH 95:5→90:10→80:20) provided, in order of elution, trans-3-((3,5-dimethylphenyl)methyloxy)-2-phenylpiperidine as a colourless oil. $^1$H NMR ($CDCl_3$) δ7.5–7.24 (m), 6.80 (s), 6.50 (s), 4.20 (d, J=11 Hz), 3.98 (d, J=11 Hz), 3.48 (d, J=8.4 Hz), 3.32 (ddd, J=4.2, 9.8, 9.8 Hz), 3.08 (m), 2.70 (ddd, J=2.8, 12.6, 12.6 Hz), 2.10 (m), 2.19 (s), 1.84–1.4 (m), and cis-3-((3,5-dimethylphenyl)methyloxy)-2-phenylpipieridine as a colourless oil. $^1$H NMR ($CDCl_3$) δ7.4–7.2 (m), 6.55 (s), 6.31 (s), 4.33 (d, J=12.2 Hz), 4.10 (d, J=12.2 Hz), 3.78 (s), 3.63 (s), 3.26 (app. dt, J=2.16, 2.16, 12.5 Hz), 2.82 (ddd, J=3.0, 3.0, 12.6 Hz), 2.20 (s), 1.86 (m), 1.62 (m), 1.48 (m). m/z ($CI^+$) 296(MH).

Acetyl chloride (0.26 ml, 3.66 mmol) was added dropwise with stirring to anhydrous methanol (3.7 ml) and the resultant solution was added to a solution of cis-3-((3,5-dimethylphenyl)methyloxy)- 2-phenylpiperidine (360 mg, 1.22 mmol) in anhydrous methanol (1 ml). The solvent was removed in vacuo, and the residue recrystallised from ethyl acetate-methanol to provide cis-3-((3,5-dimethylphenyl)methyloxy)-2-phenyl piperidine hydrochloride salt as a crystalline, white solid, m.p.=200°–225° C. (decomp). $^1$H NMR (360 MHz, DMSO-$d_6$) δ7.44 (m), 6.82 (2), 6.56 (2), 4.49 (2), 4.41 (d, J=12.3 Hz), 4.09 (d, J=12.3 Hz), 3.80 (s), 3.05 (t, J= 14.7 Hz), 2.14 (s), 1.90 (m), 1.72 (m); m/z ($CI^+$) 296 (MH); Analysis: Found: C, 72.36; H, 7.91; N, 4.31. Calcd. for $C_{20}H_{26}NOCl$; C, 72.38; H, 7.90; N, 4.22%.

EXAMPLE 3:
cis-3-((3,5-Dimethylphenyl)methyloxy)-1-methyl-2-phenylpiperidine A solution of cis-3-((3,5-dimethylphenyl)methyloxy)-2-phenylpiperidine (220 mg, 0.75 mmol, Example 2) and acetic acid (0.212 ml) in dry methanol (6 ml) was cooled to 0° C. and sodium cyanoborohydride (96 mg, 1.5 mmol) was added followed by formaldehyde (38% aq. solution, 0.15 ml). The reaction mixture was stirred at 23° C. for 18 h, then the solvent was removed in-vacuo and the residue partitioned between dichloromethane and 2M sodium hydroxide. The layers were separated, and the aqueous phase extracted with dichloromethane (2×20 ml). The combined organic extracts were washed with water then brine, then dried ($K_2CO_3$) and concentrated to leave a clear oil. Purification on silica-gel ($CH_2Cl_2$/MeOH/$NH_3$ 97:3:0.5 then $CH_2Cl_2$/MeOH 90:10) provided the title compound as a clear, colourless oil. $^1$H NMR ($CDCl_3$) 7.42 (m), 7.30 (m), 6.77 (s), 6.54 (s), 4.27 (d, J=12.2 Hz), 4.04 (d, J=12.2 Hz), 3.42 (s), 3.07 (m), 2.91 (d, J=1.9 Hz), 2.17 (s), 2.10 (m) 2.04 (s), 1.56 (m), 1.39 (m). MS (CI) m/z 310 (MH).

EXAMPLE 4:
cis-3-((3,5-Bis(trifluoromethyl)phenyl)methyloxy)-2-phenylpiperidine hydrochloride salt The title compound was prepared from 1-t-butyloxycarbonyl- 3-hydroxy-2-phenylpiperidine (Example 2c) and 3,5-bis(trifluoromethyl)benzylbromide in an analogous manner to that described in Example 2d,e, m.p.=170°–210° C. (decomp.). $^1$H NMR (360 MHz, DMSO) δ7.95 (s), 7.81 (s), 7.47 (m), 7.37 (m), 4.78 (d, J=13.3 Hz), 4.56 (s), 4.32 (d, J=13.3 Hz), 3.96 (s), 3.10 (t. J=12.7 Hz), 2.23 (d, J=13.0 Hz), 2.00–1.64 (m); m/z ($CI^+$) 404(MH); Analysis: Found: C, 54.08; H, 4.47; N, 3.13. Calcd. for $C_{20}H_{20}NOF_6Cl.0.25H_2O$ C, 54.06; H, 4.65; N, 3.15%.

EXAMPLE 5: (+)-cis-3((3,5-Bis(trifluoromethyl)phenyl)methyloxy)-2-phenylpiperidine hydrochloride salt a) The mixture of cis- and trans-isomers of 3-hydroxy-2-phenylpiperidine (Example 2b) and 4-toluenesulfonic acid monohydrate was crystallized from methanol/ethyl acetate to give cis-3-hydroxy-2-phenylpiperidinium tosylate, m.p. 266°– 267° C.

b) The tosylate salt (Example 5a) was dissolved in a mixture of ethyl acetate and 10% aqueous $Na_2CO_3$ with warming. The organic phase was washed with saturated brine, dried ($K_2CO_3$) and evaporated to give crystalline cis-3-hydroxy-2-phenylpiperidine, m.p. 110°–110.5° C.

c) cis-3-Hydroxy-2-phenylpiperidine (Example 5b) and (−)dibenzoyltartrate were dissolved in methanol and crystallized by addition of ethyl acetate. The solid was recrystallised from hot methanol to give the hemi dibenzoyltartrate salt m.p. 223°–224° C. This was liberated from the salt as described above (Example 5b) to give the single enantiomer (+)cis-3-hydroxy-2-phenylpiperidine, m.p. 93°–95° C. $[\alpha]^{23}_D$=+98.5° (c=1, MeOH). The mother liquors were converted to the free base as described in Example 5b and by crystallization using (+)dibenzoyltartrate in an analogous manner to that described above gave (−)cis-3-hydroxy-2-phenylpiperidine, m.p. 93°–95° C. $[\alpha]^{23}_D$=−97.2°(c=1, MeOH.

d) (+)cis-3-hydroxy-2-phenylpiperidine was treated analogously to that described in Example 2c, d, e to give (+)-cis-3-((3,5(bis-trifluoromethyl)phenyl)methyloxy-2-phenylpiperidine hydrochloride salt. m.p.=215°–216° C. $[\alpha]^{23}_D$=87.3°(c=1, MeOH). $^1$H NMR (360MHx, DMSO-$d_6$) δ7.95 (s), 7.81 (s), 7.47 (m), 7.37 (m), 4.78 (d, J=13.3 Hz), 4.56 (s), 4.32 (d, J=13.3 Hz), 3.96 (s), 3.10 (t, J=12.7 Hz), 2.23 (d, J=13.0 Hz), 2.00–1.64 (m); m/z ($CI^+$) 404(MH); Analysis: Found: C, 54.52; H, 4.60; N, 3.11. Calcd. for $C_{20}H_{20}NOF_6Cl$; C, 54.62; H, 4.58; N, 3.18%.

EXAMPLE 6:
cis-3-((3,5-Bis(trifluoromethyl)phenyl)methyloxy)-1-(carbomethoxy)methyl-2-phenylpiperidine cis 3-((3,5-Bis(trifluoromethyl)phenyl)methyloxy)-2-phenylpiperidine was liberated from the hydrochloride salt (Example 4, 1 g) by partitioning between ethyl acetate and 2M sodium hydroxide. The organic phase was washed successively with water, saturated brine, dried ($MgSO_4$) and evaporated in vacuo. To a solution of the residual oil in tetrahydrofuran (20 ml) was added triethylamine (0.4 ml) and methyl bromoacetate and the solution was heated at reflux under an atmosphere of nitrogen for 16 h. To the cooled solution was added ethyl acetate and water and the organic phase washed further with water and dried ($MgSO_4$). After the solvent had been removed in vacuo the residue was chromatographed on silica gel eluting with ethyl acetate/petroleum ether (3:10). The product which was obtained was recrystallized from diethyl ether/petroleum ether to give the title compound, m.p.=81°–83° C. Found: C, 57.35; H, 4.98; N, 2.84; $C_{23}H_{23}F_6NO_3.0.1(H_2O)$ requires C, 57.71; H, 4.86; N, 2.93%. m/z (CI$^+$) 476(MH).

EXAMPLE 7:
cis-3-((3,5,-Bis(trifluoromethyl)phenyl)methyloxy)-1-(carboxamido)methyl, 2-phenylpiperidine A solution of the methyl ester (Example 6, 0.6 g) in methanol (20 ml) was saturated with ammonia at 0° C., sealed and stored at 5° C. for 72 h. The solution was evaporated to dryness and the residue chromatographed on silica gel eluting with ethyl acetate/petroleum ether (bp= 60°–80° C.) (1:1). The product which eluted was concentrated and recrystallized from diethyl ether/ethyl acetate to give the title compound, m.p.=150°–152 ° C. Found: C, 56.71; H, 4.79; N, 5.87; $C_{22}H_{22}F_6O_2N_2.0.1(H_2O)$ requires C, 56.98; H, 4.80; N, 6.04%. m/z (CI$^+$) 461(MH), m/z (CI$^-$) 459(M-H).

EXAMPLE 8:
(+)-cis-3-((3,5-Bis(trifluoromethyl)phenyl)methyloxy)-1-(carbomethoxy)methyl-2-phenylpiperidine The title compound was prepared from (+)-cis-3-((3,5-bis(trifluoromethyl)phenyl)methyloxy)-2-phenylpiperidine (Example 5) by a procedure analogous to that described in Example 6, m.p.=60°–70° C., $[\alpha]^{24}_D$=+132.3° (c=1, MeOH). Found: C, 58.31; H, 4.90; N, 2.94. $C_{23}H_{23}F_6NO_3$ requires C, 58.11; H, 4.88; N, 2.95%.

EXAMPLE 9:
(+)-cis-3-((3,5-Bis(trifluoromethyl)phenyl)methyloxy)-1-(carboxamido)methyl-2-phenylpiperidinium hydrochloride The title compound was prepared from (+)-cis-3-((3,5-Bis(trifluoromethyl)phenyl)methyloxy)-1-(carbomethoxy)methyl-2-phenylpiperidine (Example 8) using a procedure analogous to that described in Example 7, and crystallized finally as the hydrochloride salt, m.p.=192°–3° C. $[\alpha]^{24}_D$=+80.4° (c=1, MeOH). Found: C, 53.27; H, 4.68; N, 5.56. $C_{22}H_{22}F_6O_2N_2.HCl$ requires C, 53.18; H, 4.67; N, 5.64%.

EXAMPLE 10:
(+)-cis-3-((3,5-Bis(trifluoromethyl)phenyl)methyloxy)-1-methyl-2-phenylpiperidine The title compound was prepared from (+)-cis-3-((3,5-bis(trifluoromethyl)phenyl)methyloxy)-2-phenylpiperidine hydrochloride (Example 5) by isolation of the free base (by extraction into ethyl acetate from 10% $Na_2CO_3$ solution) and alkylation using a procedure analogous to that described in Example 3, m.p.=40°–42° C.: $[\alpha]^{26}_D$=+149° (c=0.56, MeOH); Found: C, 59.97; H, 4.95; N, 3.36. $C_{21}H_{21}NOF_6.0.1(H_2O)$ requires C, 60.17; H, 5.10; N, 3.34%.

EXAMPLE 11:
(−)-cis-3-((3,5-Bis(trifluoromethyl)phenyl)methyloxy)-2-phenyl piperidine hydrochloride salt The title compound was prepared from (−)-cis-3-hydroxy-2-phenyl piperidine (Example 5c) by a procedure analogous to that described in Example 5d, m.p.=215°–216° C. $[\alpha]_D^{23}$=−86.9° (c=1, MeOH). Found: C, 54.44; H, 4.54; N, 3.11. Calcd for $C_{20}H_{19}NOF_6.HCl$; C, 54.62; H, 4.58; N, 3.18%.

EXAMPLE 12:
trans-((3.5-Dimethylphenyl)methyloxy)-2-phenyl piperidine hydrochloride salt The title compound was prepared from trans-1-t-butyloxycarbonyl-3-hydroxy-2-phenylpiperidine (Example 2c) by a procedure analogous to that described in Example 2d, e, m.p.=210°–235° C.

EXAMPLE 13:
trans-3-((3,5-Bis(trifluoromethyl)phenyl)methyloxy)-2-phenyl piperidine hydrochloride salt The title compound was prepared in an analogous manner to that described in Example 4 and separated from the cis-isomer by chromatography on silica gel and crystallisation as the hydrochloride salt, m.p.=216°–226° C. Found: C, 54.38; H, 4.54; N, 3.12. Calcd for $C_{20}H_{19}NOF_6.HCl$; C, 54.62; H, 4.58; N, 3.18%.

EXAMPLE 14:
(2S,3S)-3-((3,5-Bis(trifluoromethyl)phenyl)methyloxy)-1,1-dimethyl2-phenyl piperidinium iodide The title compound was prepared from the N-methyl amine (0.24 g, Example 10) with methyl iodide (0.178 ml) in diethyl ether (3 ml). After 62 h the white solid which formed was isolated by filtration and washed with ether, m.p.=204°–205° C. Found: C, 46.74; H, 4.29; N, 2.41. Calcd for $C_{22}H_{24}NOF_6I.0.3H_2O$; C, 46.79; H, 4.39; N, 2.48%.

EXAMPLE 15:
(2S,3S)-1-Acetyl-3-((3,5-bis(trifluoromethyl)phenyl)methyloxy)-2-phenyl piperidine To a solution of (+)-cis-3-((3,5-bis(trifluoromethyl)phenyl)methyloxy)-2-phenyl piperidine prepared from hydrochloride salt (Example 5, 1.0 g) by partitioning between aqueous sodium carbonate and dichloromethane) in dry dichloromethane (5 ml) was added pyridine (0.67 ml), acetic anhydride (0.79 ml) and 4,4-dimethylamine pyridine (10 mg). After the solution had been stirred for 3 h at 23° C., saturated sodium bicarbonate solution was added and the organic phase dried ($MgSO_4$), evaporated in vacuo and chromatographed on silica gel to give the title compound as an oil. Found: C, 59.51; H, 4.90; N, 3.09. Calcd for $C_{22}H_{21}NO_2F_6$; C, 59.33; H, 4.75; N, 3.14%.

EXAMPLE 16:
(2S,3S)-1-Formyl-3-((3,5-bis(trifluoromethyl) phenyl)methyloxy)-2-phenyl piperidine The title compound was prepared from (+)-cis-3-((3,5-bis(trifluoromethyl)phenyl)methyloxy)-2-phenyl piperidine prepared from the hydrochloride salt, Example 5)(0.5 g) and formic-acetic anhydride (prepared from 90% formic acid (1.5 ml) and acetic anhydride (3 ml) at 60° C. for 30 minutes) in tetrahydrofuran for 48 h at 23° C. The solvent was evaporated in vacuo and the residue partitioned between diochloromethane and saturated aqueous sodium bicarbonate solution, dried (MgSO$_4$), concentrated in vacuo and chromatographed on silica gel to give the title compound as an oil. Found: C, 57.79; H, 4.39; N, 3.13. Calcd for $C_{21}H_{19}NO_2F_6 \cdot 0.3(H_2O)$, C, 57.75; H, 4.52; N, 3.21%.

EXAMPLE 17:
(2S,3S)-1-Benzyl-3-((3,5-bis(trifluoromethyl) phenyl)methyloxy)-2-phenylpiperidine Benzyl bromide (0.134 ml) was added to a mixture of (+)-cis-3-((3,5-bis(trifluoromethyl)phenyl)methyloxy)-2-phenyl piperidine (prepared from the hydrochloride salt, Example 5) (0.5 g) and potassium carbonate (0.468 g) in N,N-dimethylformamide (2 ml) and the mixture stirred at 23° C. for 2.5 h. Water (20 ml) was added and the mixture extracted with ethyl acetate (3×15 ml). The combined organic extracts were washed with water (1×10 ml) and brine (1×10 ml) then dried (K$_2$CO$_3$) and concentrated to leave an oil. Purification on silica gel eluting with hexanes-ethyl acetate (19:1 then 9:1 then 4:1 then 1:1) provided the title compound as a solid, m.p.=89°–93° C. Found: C, 66.11; H, 5.25; N, 2.81. Calcd. for $C_{27}H_{25}NOF_6$; C, 65.71; H, 5.11; N, 2.84%.

EXAMPLE 18: (2S, 3S)-3-(3,5-Bis(trifluoromethyl)phenyl)methyloxy)-1-(1-carbomethoxy)ethyl-2-phenyl piperidine The title compound was prepared in a manner analogous to that described in Example 17 with methyl DL-2-bromopropionate and potassium carbonate in N,N-dimethylformamide at 80° C. for 2 h. Purification by chromatography on silica gel provided diastereoisomer A as a solid, m.p.= 65°–66° C. Found: C, 58.87; H, 5.12; N, 2.94. Calcd for $C_{24}H_{25}NO_3F_6$; C, 58.89; H, 5.15; N, 2.86%, and diastereoisomer B as an oil, $^1$H NMR (360 MHz, CDCl$_3$) δ7.7 (s), 7.5 (m), 7.3 (m), 4.45 (d), 4.06 (d), 3.77–3.47 (m), 3.06 (br d), 2.59 (t), 2.10 (m), 1.54 (m), 1.03 (d), m/z (CI$^+$) 490(MH).

EXAMPLE 19: (2S, 3S)-3(3,5-Bis(trifluoromethyl)phenyl)methyloxy)-1-(carboxamido)ethyl-2-phenylpiperidinium hydrochloride A solution of the methyl ester (diastereoisomer B, Example 18) in methanol was added to liquid ammonia at −50° C. then heated to 150° C. (60 Bar) for 48 h. The solution was evaporated to dryness and the residue chromatographed on silica gel eluting with hexanes/ethyl acetate (4:1) then ethyl acetate/methanol (9:1). The title compound was crystallised finally as the hydrochloride salt, m.p.= 112°–117° C.

EXAMPLE 20:
cis-3-(3,5-Bis(trifluoromethyl)phenyl)methyloxy-6-methyl-2-phenyl piperidinium hydrochloride Magnesium metal (1.03 g, 42.8 mmol), 6 ml of a solution of 4-bromo-1-butene (5.5 g, 40.8 mmol) in dry tetrahydrofuran (30 ml) and 1,2-dibromoethane (2 drops) were gently warmed until reaction commenced. The remainder of the bromoalkene solution was then added dropwise over 10 min. The reaction mixture was stirred at 23° C. for 1 h, then added to a cooled (−10° C.) solution of N-Boc phenyl glycine aldehyde (3.2 g) in dry tetrahydrofuran (20 ml), the mixture was allowed to warm to 23° C., stirred for 1 h then quenched by the addition of saturated aqueous ammonium chloride solution. The layers were separated, the aqueous phase was extracted with ethyl acetate (3×60 ml ), the combined organic phases were washed with brine (1×50 ml), dried (MgSO$_4$) and concentrated to leave N-Boc- 2-hydroxy-1-phenyl-hex-5-enyl-1-amine as a pale yellow oil. $^1$H NMR (250 MHz, CDCl$_3$) δ7.4–7.2 (m), 5.9–5.7 (m), 5.35 (d), 5.1–4.9 (m), 4.65 (br m), 3.85 (m), 2.2 (m), 1.65 (m), 1.45 (s).

Sodium hydride (80% in oil, 161 mg) was added to a solution of N-Boc-2-hydroxy-1-phenyl-hex-5-enyl-1-amine (1.2 g) and 3,5-bis-trifluoromethylbenzylbromide (1.13 ml) in dry N,N-dimethylformamide (5 ml). The reaction mixture was stirred for 16 h at 23° C., then diluted with water (50 ml) and extracted with ethyl acetate (3×40 ml). The combined organic phases were washed with water (1×) and brine (1×) then dried (MgSO$_4$) and concentrated to leave an oil. Purification by chromatography on silica gel (hexanes/ethyl acetate 9:1 then 4:1 then 1:1) provided N-Boc-2-((3,5-bis(trifluoromethyl)phenyl)methyloxy)- 1-phenyl-hex-5-enyl-1-amine as a pale yellow oil. $^1$H NMR (360 MHz, CDCl$_3$) δ7.78 (s), 7.72 (s), 7.35–7.25 (m), 5.72 (m), 4.95 (m), 4.65 (d), 4.50 (d), 4.05 (d), 3.60 (q), 2.11 (m), 1.66 (m).

A solution of N-Boc-2-((3,5-bis(trifluoromethyl)phenyl) methyloxy)-1-phenyl-hex-5-enyl-1-amine (0.3 g) and mercuric acetate (0.37 g) in dry tetrahydrofuran (6 ml) was stirred at 50° C. under N$_2$ for 15 h. The solvent was removed in vacuo and the residue dissolved in chloroform (20 ml) and mixed thoroughly with saturated potassium chloride solution (10 ml). The layers were separated, and the aqueous phase extracted with chloroform (1×15 ml). The combined organic phases were dried (MgSO$_4$) and concentrated to leave a yellow oil.

The crude product was dissolved in dry N,N-dimethylformamide (2 ml) and added dropwise to a stirred suspension of sodium borohydride (0.042 mg, 11 mmol) in dry N,N-dimethylformamide. The reaction mixture was stirred for 0.5 h at 23° C. then diluted with diethyl ether and filtered through a pad of Hi-flo. The filtrate was poured into water (30 ml) and extracted with ethyl acetate (3×20 ml). The combined organic extracts were washed with saturated aqueous sodium bicarbonate solution (1×15 ml) and brine (1×15 ml) then dried (MgSO$_4$) and concentrated to leave an orange-yellow oil. Purification by chromatography on silica gel eluting with hexanes/ethyl acetate (19:1) provided 3-(( 3,5-bis(trifluoromethyl)phenyl)methyloxy-1-(t-butyloxycarbonyl)-6-methyl-2phenylpiperidine as a clear, viscous oil.

This material was dissolved in trifluoroacetic acid (2 ml) under nitrogen, after 10 min the trifluoroacetic acid was evaporated in vacuo and the residue partitioned between 2M sodium hydroxide and dichloromethane. The layers were separated, and the aqueous phase extracted with dichloromethane (2×20 ml). The combined organic phases were dried (K$_2$CO$_3$) and concentrated to leave an oil, which was purified by chromatography on silica gel eluting with hexanes/ethyl acetate (4:1 then 1:1) to provide 3-(( 3,5-bis(trifluoromethyl)phenyl)methyloxy-6-methyl-2-phenyl piperidine as a clear, viscous oil. The title compound was finally crystallised as the hydrochloride salt, m.p.=218°–220° C. Found: C, 55.15; H, 4.79; N, 3.33; Calcd. for $C_{21}H_{22}NOClF_6$ C, 55.58; H, 4.89; N, 3.09%.

EXAMPLE 21:
cis-3-((3,5-Bis(trifluoromethyl)phenyl)methyloxy)-2-(2-chlorophenyl)piperidine a) Methyl-4-nitrobutyrate and 2-chlorobenzaldehyde were reacted in an analogous manner to that described in Example 2a to give 6-(2-chlorophenyl)-5-nitro-2-oxopiperidine. $^1$H NMR (360 MHz, CDCl$_3$) δ2.00–2.18 (1H, m), 2.42–2.61 (3H, m), 4.80–4.87 (1H, m), 5.91 (1H, d), 6.41 (1H, s), 7.17–7.42 (4H, m).

b) Sodium methoxide (0.25 g) was added to a suspension of 5-nitro-2-oxo-6-(2-chlorophenyl)piperidine (1.0 g) in methanol (10ml) to give solution (A).

To a cooled (0° C.) solution of ammonium acetate (9.61 g, 125 mmol) in degassed water (30 ml) under nitrogen was added titanium trichloride (13% solution in 20% HCl, 29.6 ml, 23.4 mmol) over 20 min. Solution (A) was added over 20 min. The resulting mixture was stirred at 23° C. for 2 hrs, then extracted with ethyl acetate (150 ml×4). The combined organic extracts were washed with brine (40 ml), then dried (MgSO$_4$) and concentrated to give 6-(2-Chlorophenyl)-2,5-dioxopiperidine. $^1$H NMR (250 MHz, CDCl$_3$) δ2.81–2.93 (4H, m), 5.4 (1H, m), 5.8 (1H, s), 7.20–7.40 (4H, m).

c) To a stirred suspension of 6-(2-chlorophenyl)-2,5-dioxopiperidine (2.50 g) in methanol (25 ml) under nitrogen at −30° C. was added, portionwise, sodium borohydride (0.21 g). After 10 rain HPLC indicated no starting material remained. The mixture was concentrated in vacuo and the residue azeotroped with toluene (2×30 ml). The crude material was cooled (0° C.) and borane-tetrahydrofuran complex (45 ml, 1.0M solution in tetrahydrofuran) was added over 25 min. When the addition was complete the mixture was heated at reflux for 16 hrs. The reaction mixture was cooled to 5° C. and quenched with methanol, then concentrated in vacuo. The residue was dissolved in ethanol (30 ml) and potassium carbonate (3.10 g) was added and t, he mixture was heated at reflux for 6 hrs. The solvent was removed in vacuo and the residue was partitioned between ethyl acetate (50 ml) and water (100 ml). The aqueous layer was extracted with ethyl acetate (3×50 ml). The combined organic extracts were dried (MgSO$_4$) and concentrated in vacuo. $^1$H NMR (360 MHz, DMSO) δ1.66–1.70 (1H, m), 1.82–2.12 (3H, m), 2.28 (3H, s), 3.31 (1H, m), 4.04 (1H, s), 4.64 (1H, d), 5.6 (1H, s), 7.08 (2H, d), 7.4–7.61 (6H, m). The residue was dissolved in methanol (20 ml) and p-toluene sulphonic acid (2.13 g) was added. Evaporation in vacuo and recrystallisation from ethyl acetate/methanol gave cis-2-(2-chlorophenyl)-3hydroxypiperidine tosylate salt.

d) The product of part c) was dissolved in a mixture of dichloromethane and 10% aqueous sodium carbonate solution with gentle warming. The organic phase was washed with saturated brine, dried (MgSO$_4$) and concentrated to give cis-2-(2-chlorophenyl)-3-hydroxypiperidine. Di-t-butyldicarbonate was added to cis-2-(2-chlorophenyl)-3-hydroxypiperidine in an analogous manner to that described in Example 2c to give cis-1-t-butloxycarbonyl-2-(2-chlorophenyl)- 3hydroxypiperidine. $^1$H NMR (250 MHz, CDCl$_3$) δ1.24 (9H, s), 1.40–2.10 (4H, m), 3.40–3.56 (1H, m), 4.08–4.22 (1H, m), 4.26–4.36 (1H, m), 5.40 (1H, d), 7.18–7.42 (4H, m).

e) The product of part d) and 3,5-bis(trifluoromethyl)benzyl bromide were added together in an analogous manner to that described in Example 2d to give cis3-((3,5-bis(trifluoromethyl)phenyl)methyloxy)- 1-t-butyloxycarbonyl-2-(2-chlorophenyl)piperidine. $^1$H NMR (360 MHz, CDCl$_3$) δ1.22 (9H, s), 1.62–2.20 (4H, m), 3.38–3.47 (1H, ddd), 4.16–4.20 (2H, m), 4.21–4.25 (1H, d), 4.46–4.50 (1H, d), 7.13–7.38 (4H, m), 7.40 (2H, s), 7.64 (1H, s). m/z (CI$^+$) 538, 540.

f) The product of part e) was treated with trifluoroacetic acid in an analogous manner to that described in Example 2e and crystallised as the oxalate salt, m.p.=165° C. $^1$H NMR (360 MHz, DMSO-d$_6$) δ1.64–1.92 (3H, m), 2.21–2.30 (1H, m), 3.20–3.42 (2H, m), 4.00 (1H, s), 4.30–4.34 (1H, d), 4.78–4.80 (1H, d), 4.80–4.84 (1H, s), 7.38–7.40 (2H, m), 7.45–7.51 (1H, m), 7.57–7.61 (1H, m), 7.75 (2H, s), 7.94 (1H, s). Found: C, 48.57; H, 3.92; N, 2.51. C$_{20}$H$_{18}$ClF$_6$NO.C$_2$O$_4$H$_2$H$_2$O requires: C, 48.41; H, 4.06; N, 2.57%.

EXAMPLE 22:
cis-3-((3,5-Bis(trifluoromethyl)phenyl)methyloxy)-2-(3-chlorophenyl)piperidine hydrochloride salt a) Methyl-4-nitrobutyrate and 3-chlorobenzaldehyde were reacted in an analogous manner to that described in Example 2a to give 2-(3-chlorophenyl)-3-nitro-6-oxopiperidine, m.p.=131°–133° C. $^1$H NMR (360 MHz, CDCl$_3$) δ2.26–2.36 (1H, m), 2.50–2.72 (3H, m), 4.66–4.71 (1H, m), 5.24–5.28 (1H, d), 6.57 (1H, s), 7.17–7.40 (4H, m).

b) The product of part a) was treated analogously to that described in Example 2b to give 2-(3-chlorophenyl)-3,6-dioxo piperidine, m.p.=144°–147° C. $^1$H NMR (250 MHz, CDCl$_3$) δ2.8 (4H, m), 5.0 (1H, d), 6.4 (1H, s), 7.22–7.42 (4H, m).

c) The product of part b) was treated analogously to that described in Example 21c to give cis-2-(3-chlorophenyl)-3-hydroxypiperidine tosylate salt, m.p.>250° C. $^1$H NMR (250 MHz, DMSO-d$_6$) δ1.60–2.07 (4H, m), 2.28 (3H, s), 3.00–3.11 (1H, m), 4.02 (1H, s), 4.62–4.66 (1H, d), 5.96 (1H, s), 7.10–7.20 (2H, d), 7.41–7.59 (6H, m).

d) The product of part c) was treated analogously to that described in Example 21d to give cis-1-t-butyloxycarbonyl-2-(3chlorophenyl)-3-hydroxypiperidine as a clear, viscous oil. 1H NMR (360 MHz, CDCl$_3$) δ1.40 (9H, s), 1,61–1.90 (4H, m), 2.88–3.01 (1H, ddd), 3.93–3.99 (1H,dd), 4.03–4.10 (1H, m), 5.33 (1H, d), 7.20–7.26 (2H, m), 7.34–7.38 (1H, m), 7.47–7.52 (1H, m). m/z (CI$^-$) 310, 312; m/z (CI$^+$) 312, 314.

e) The product of part d) and 3,5-bis(trifluoromethyl)benzylbromide were treated in an analogous manner to that described in Example 2d to give cis-3-((3,5-bis(trifluoromethyl)phenyl)methyloxy)- 1-t-butyloxycarbonyl-2-(3-chlorophenyl)piperidine. $^1$H NMR (250 MHz, CDCl$_3$) δ1.24–1.30 (1H, m), 1.47 (9H, s), 1.60–2.00 (3H, m), 2.67–2.80 (1H,ddd), 3.81–4.01 (2H, m), 4.8 (2H, s), 5.61–5.67 (1H, d), 7.23–7.27 (2H, m), 7.39–7.44 (1H, m), 7.6 (1H, s), 7.78 (2H, s), 7.8 (1H, s).

f) The product of part e) was treated in an analogous manner to that described in Example 2e to give cis-3-((3,5-bis(trifluoromethyl)phenyl)methyloxy)- 2-(3-chlorophenyl)piperidine hydrochloride salt, m.p.=158° C. $^1$H NMR (360 MHz, DMSO-d$_6$) δ1.70–1.96 (4H, m), 2.19–2.28 (1H, m), 3.02–3.13 (1H, m), 3.84 (1H, s), 4.35–4.39 (2H, d), 4.60 (1H, s), 4.79–4.85 (2H, d), 7.39–7.44 (3H, m), 7.58 (1H, s), 7.84 (2H, s), 7.97 (1H, s), 9.2 (br s), 10.05 (br s). Found: C, 50.44; H, 4.13; N, 3.01. C$_{20}$H$_{18}$ClF$_6$NO.HCl requires C, 50.65; H, 4.04; N, 2.95%. m/z (CI$^+$), 438, 440.

EXAMPLE 23:
cis-3-((3,5-Bis(trifluoromethyl)phenyl)methyloxy)-2-(4-chlorophenyl)piperidine hydrochloride salt a) Methyl-4-nitrobutyrate and 4-chlorobenzaldehyde were treated in an analogous manner to that described in Example 2a to give 2-(4-chlorophenyl)-3-nitro-6-oxopiperidine. $^1$H NMR (360 MHz, CDCl$_3$) δ2.24–2.38 (1H, m), 2.51–2.70 (3H, m), 4.60–4.69 (1H, m), 5.20 (1H, d), 6.82 (1H, s), 7.22–7.26 (2H, d), 7.36–7.40 (2H, d).

b) The product of part a) was treated in an analogous manner to that described in Example 2b to give 2-(4-chlorophenyl)-3,6-dioxopiperidine. $^1$H NMR (260 MHz, CDCl$_3$) δ2.8 (4H, s), 5.0 (1H, d), 6.4 (1H, s), 7.22–7.46 (4H, q).

c) The product of part b) was treated analogously to that described in Example 21c to give cis-2-(4-chlorophenyl)-3-hydroxypiperidine tosylate salt. $^1$H NMR (360 MHz, DMSO-d$_6$) δ1.62–2.13 (4H, m), 2.30 (3H, s), 3.01–3.26 (2H, m), 4.00 (1H, s), 4.28 (1H, s), 5.00–5.60 (b), 7.11–7.15 (2H, d), 7.44–7.56 (6H, m), 8.60–9.10 (b).

d) The product of part c) was treated analogously to that described in Example 21d to give cis-1-t-butyloxycarbonyl-2-(4-chlorophenyl)-3-hydroxypiperidine, m.p.=95°–96° C., m/z (CI$^+$) 312, 314.

e) The product of part d) (0.7 g, 2.25 mmol) was dissolved in ethylene glycol dimethyl ether (1 ml). 0.5M potassium bis(trimethylsilyl)amide (4.9 ml) was added. The mixture was stirred at 23° C. for 20 min, then 3,5-bis(trifluoromethyl)benzylbromide (0.50ml) was added. After stirring for 18 hr the solvent was removed in vacuo, and the residue partitioned between ethyl acetate and water. The organic phase was dried (MgSO$_4$). The residue after removal of solvent in vacuo, was chromatographed on silica gel using hexane/ethyl acetate (9:1) as eluant to give cis-3-(3,5-bis-(trifluoromethyl)phenyl)methyloxy)-1-t-butyloxycarbonyl-2-(4-chlorophenyl)piperidine, $^1$H NMR (360 MHz, CDCl$_3$) δ1.46 (9H, s), 1.58–2.04 (4H, m), 2.66–2.76 (1H, ddd), 3.82–3.98 (2H, m), 4.72 (2H, s), 6.64 (1H, s), 7.28–7.32 (2H, d), 7.46–7.50 (2H, d), 7.70 (2H, s), 7.80 (1H, s). m/z (CI$^+$) 438, 540.

f) The product of part e) was dissolved in diethyl ether (5 ml). Saturated hydrogen chloride in diethyl ether (10 ml) was added. The mixture was stirred at 23° C. under nitrogen for 2.5 hrs, then concentrated in vacuo. Recrystallisation from ethyl acetate/diethyl ether provided cis-3-(3,5-bis(trifluoromethyl)phenyl)methyloxy)- 2-(4chlorophenyl)piperidine hydrochloride salt, m.p.=202° C. $^1$H NMR (360 MHz, DMSO-d$_6$) δ1.65–1.95 (3H, m), 2.20–2.26 (1H, m), 3.02–3.14 (1H, ddd), 3.21–3.37 (1H, m), 3.94 (1H, s), 4.36–4.42 (1H, d), 4.6 (1H, s), 4.78–4.80 (1H, d), 7.40–7.47 (4H, m), 7.78 (2H, s), 8.00 (1H, s). m/z (CI$^+$) 438, 446. Found: C, 48.97; H, 3.98; N, 2.80. C$_{20}$H$_{19}$Cl$_2$F$_6$NO.H$_2$O, requires C, 48.79; H, 4.29; N, 2.84.

EXAMPLE 24:
cis-3-(3,5,-Bis(trifluoromethyl)phenyl)methyloxy)-2-(4-methylphenyl)piperidine hydrochloride salt a) Methyl-4-nitrobutyrate and 4-methylbenzaldehyde were treated in an analogous manner to that described in Example 2a to give 2-(4-methylphenyl)-3-nitro-6-oxopiperidine. $^1$H NMR (360 MHz, CDCl$_3$) δ2.4 (3H, s), 2.47–2.65 (4H, m), 4.62–4.67 (1H, m), 5.2 (1H, d), 6.11 (1H, s), 7.2 (4H, q).

b) The product of part a) was treated in an analogous manner to that described in Example 2b to give 2-(4-methylphenyl)-3, 6-dioxopiperidine. NMR (360 MHz, CDCl$_3$) δ2.17 (3H, s), 2.24–2.81 (4H, m), 4.9 (1H, d), 6.2 (1H, s), 7.21 (4H, q).

c) The product of part b) was treated analogously to that described in Example 21c to provide cis-2-(4-methylphenyl)-3-hydroxypiperidine tosylate salt. $^1$H NMR (free base, 250 MHz, CDCl$_3$) δ1.21–1.43 (2H, m), 1.60–1.83 (2H, m), 2.13 (3H, s), 2.47–2.65 (1H, ddd), 3.01 (1H, m), 3.57 (1H, s), 3.83 (1H, s), 7.00–7.20 (4H, q). d) The product of part c) was treated analogously to that described in Example 2d to give cis-1-t-butyloxycarbonyl-3-hydroxy-2-(4-methylphenyl)piperidine. $^1$H NMR (360 MHz, CDCl$_3$) δ1.27 (9H, s), 1.61–1.80 (4H, m), 2.11 (3H, s), 2.91–2.99 (1H, ddd), 3.91–4.01 (2H, m), 5.22 (1H, d), 7.02 (2H, d), 7.16 (2H, d). m/z (CI$^+$) 292.

e) The product of part d) was treated in an analogous manner to that described in Example 23e to give cis-3-((3, 5-bis(trifluoromethyl)phenyl)methyloxy)- 1-t-butyloxycarbonyl-2-(4-methylphenyl)piperidine. $^1$H NMR (250 MHz, CDCl$_3$) δ1.41 (9H, s), 1.60–1.69 (2H, m), 7.89–2.01 (2H, m), 2.17 (3H, s), 2.65–3.03 (1H, ddd), 3.87–3.99 (2H, m), 4.74 (2H, q), 5.71 (1H, d), 7.10 (2H, d), 7.21 (2H, d), 7.65 (2H, s), 7.81 (1H, s).

f) cis-3-((3,5-Bis(trifluoromethyl)phenyl)methyloxy)-1-t-butyloxycarbonyl- 2-(4-methylphenyl)piperidine was treated analogously to that described in Example 23f to give cis-3-(3-(3,5-bis(trifluoromethyl)phenyl)methyloxy-2-(4methylphenyl)piperidine hydrochloride salt, m.p.=195° C. $^1$H NMR (360 MHz, DMSO-d$_6$) δ1.62–1.96 (4H, m), 2.13 (3H, s), 3.01–3.12 (1H, ddd), 3.91 (1H, s), 4.26 (1H, d), 4.47 (1H, s), 4.80 (1H, d), 7.20 (2H, d), 7.31 (2H, d), 7.80 (2H, s), 7.92 (1H, s). Found: C, 53.22; H, 4.76; N, 2.93. C$_{21}$H$_{21}$F$_6$NO.1.5HCl requires C, 53.43; H, 4.80; N, 2.97%. m/z (CI$^+$) 418.

EXAMPLE 25:
cis-3-((3,5-Bis(trifluoromethyl)phenyl)methyloxy)-2-thienyl piperidine hydrochloride salt a) Thiophene-2-carboxaldehyde (9.26 ml), methyl-4-nitrobutyrate (12.81 ml) and ammonium acetate (10.01 g) were added to ethanol (140 ml) and then the reaction mixture was refluxed for 3 h. The reaction was cooled to room temperature and ethanol was removed in vacuo. Ethyl acetate was added to the residue and insoluble material was filtered off. This afforded 5-nitro-2-oxo-6-thienylpiperidine as a yellow crystalline solid. $^1$H NMR (250 MHz, DMSO) δ2.15–2.33 (2H, m, CH$_2$), 2.34 (2H, m, CH$_2$), 5.10–5.21 (1H, m, CHNO$_2$), 5.36–5.46 (1H, m, NCH), 6.28–6.37 (1H, brs, NH), 7.01–7.14 (2H, m, ArH), 7.52–7.58 (1H, m, ArH).

b) A 13% solution of titanium trichloride in 20% hydrochloric acid (173 ml) was added to a degassed solution of ammonium acetate (100 g) in methanol (300 ml) at 0° C. under nitrogen over 20 min. A solution of sodium methoxide (1.49 g) in methanol (60 ml) was added to a suspension of 5-nitro-2-oxo-6-thienylpiperidine (5 g, Example 25a) in methanol (75 ml) and the mixture stirred for 20 min. This solution was then added dropwise to the titanium trichloride/ buffer solution at 0° C. under nitrogen. The reaction was stirred at 0° C. for 30 min and at 23° C. for 30 min. Methanol was removed in vacuo and ethyl acetate was added to the residue. The emulsion was filtered through Hi-flo and then shaken with brine. The organic phase was dried (MgSO$_4$) and concentrated in vacuo. The material was chromatographed on silica using (1:1 then 9:1) ethyl acetate in petroleum ether (60–80) as eluant to give 2,5-dioxo-6-thienylpiperidine. m/z (CI$^+$) m/z 105 (MH, 53%).

c) 2,5-Dioxo-6-thienylpiperidine (1.16 g, Example 25b) was suspended in methanol (40 ml) under nitrogen. The temperature was maintained at −40° C. using an acetonitrile/ dry ice bath while sodium borohydride (0.11 g) was added portionwise. The reaction mixture was allowed to warm to room temperature and then stirred for 1 h. Methanol was removed in vacuo and the material was azeotroped with toluene. Borane-tetrahydrofuran complex (1.0M solution) (23.8 ml) was added at room temperature and the reaction mixture was refluxed for 3 h. The reaction mixture was cooled and quenched carefully with methanol before removing the solvent in vacuo. Ethanol (60 ml) was added followed by potassium carbonate (1.64 g) and the reaction mixture was refluxed for 18 h. The solvent was removed in vacuo. 1M Sodium hydroxide solution (30 ml) and dichloromethane (30 ml) were added to the residue followed by di-t-butyldicarbonate (2.25 g). After stirring for 7 h the organic layer was separated and concentrated in vacuo. The product, cis-1-t-butyloxycarbonyl-3-hydroxy-2-thienylpiperidine, was recrystallised from hexane, m/z (CI$^+$) 283 ((MH), 82%).

d) cis-1-(t-Butyloxycarbonyl)-3-((3,5-bis(trifluoromethyl)phenyl)methyloxy)-2-thienylpiperidine was prepared from cis-1-t-butyloxycarbonyl-3-hydroxy-2-thienylpiperidine (0.97 g, Example 25c) and 3,5-bis(trifluoromethyl)benzyl bromide (0.94 ml) in an analogous manner to that described in Example 2d. The material was purified by chromatography on silica using 20% ethyl acetate in petroleum ether (60–80) as eluant. $^1$H NMR (250 MHz, CDCl$_3$) δ1.49 (9H, s, CH$_3$), 1.54–2.05 (4H, m, CH$_2$), 2.87 (1H, dt, NCH$\underline{H}$), 3.75–3.85 (1H, m, NCH$\underline{H}$), 3.97 (1H, brd, C$\underline{H}$O), 4.71 (1H, d, OCH$\underline{H}$), 4.85 (1H, d, OCH$\underline{H}$), 5.95 (1H, brs, NC$\underline{H}$), 6.98–7.03 (1H, m, thienyl H), 7.05–7.09 (1H, m, thienyl $\underline{H}$), 7.24–7.30 (1H, m, thienyl H), 7.80 (3H, s, aromatic H).

e) The trifluoroacetate salt of cis-3-((3,5bis(trifluoromethyl)phenyl)methyloxy)-2-thienylpiperidine was prepared from cis-1-t-butyloxycarbonyl-3-((3,5bis(trifluoromethyl)phenyl)methyloxy)-2-thienylpiperidine in an analogous manner to that described in Example 2e. The material was partitioned between 10% sodium hydroxide and ethyl acetate. The layers were separated and the aqueous phase was extracted twice with ethyl acetate. The combined organic phases were dried (Na$_2$SO$_4$) and concentrated to give cis-3-((3,5-bis(trifluoromethyl)phenyl)methyloxy)-2-thienylpiperidine.

A saturated solution of acetyl chloride in methanol was added to a solution of cis-3-((3,5-bis(trifluoromethyl)phenyl)methyloxy)-2-thienylpiperidine in methanol. The solvent was removed in vacuo and the residue recrystallised from diethyl ether-methanol to provide cis-3-((3,5-bis(trifluoromethyl)phenyl)methyloxy)-2-thienyl piperidine hydrochloride as a white crystalline solid. $^1$H NMR (360 MHz, DMSO) δ1.65–1.93 (3H, m, CH$_2$CH$\underline{H}$), 2.21–2.29 (1H, m, CH$\underline{H}$), 3.06–3.14 (1H, m, NCH$\underline{H}$), 3.20–3.29 (1H, d, NCH $\underline{H}$), 4.00 (1H, br s, C$\underline{H}$O), 4.61 (1H, d, J=13.1 Hz, OC$\underline{H}$H), 4.90 (1H, d, J=13.1 Hz, OCH$\underline{H}$), 7.07 (1H, dd, thienyl $\underline{H}$), 7.29–7.33 (1H, m, thienyl H), 7.58–7.62 (1H, m, thienyl H), 8.02 (1H, s, ArH), 8.11 (2H, s, ArH).

EXAMPLE 26:
cis-3-((3,5-Bis(trifluoromethyl)phenyl)methyloxy)-2-pyridyl piperidine dihydrochloride salt a) Methyl-4-nitrobutyrate (12.81 ml), ammonium acetate (10.01 g) and freshly distilled pyridine-2-carboxaldehyde were added to ethanol (140 ml) and the reaction mixture was stirred at room temperature under nitrogen for 1.5 h before being heated to reflux for 45 min. The reaction mixture was allowed to cool and left for 24 h. The brown crystals which formed were filtered off and in this way 4-nitro-2-oxo-5-pyridylpiperidine was isolated together with some residual ammonium acetate. $^1$H NMR (250 MHz, CDCl$_3$) δ2.15–2.32 (2H, m, CH$_2$), 2.47–2.69 (H, m, CH$_2$+acetate), 5.19–5.28 (1H, m, CHNO$_2$), 5.43–5.49 (1H, m, NCH), 6.70 (1H, brs, NH), 7.27–7.34 (1H, m, ArH), 7.38–7.44 (1H, m, ArH), 7.74–7.84 (1H, m, ArH), 8.60–8.67 (1H, m, ArH).

b) A 13% solution of titanium trichloride in 20% hydrochloric acid (143 ml) was added to a degassed solution of ammonium acetate (56 g) in water (200 ml) at 0° C. under nitrogen over 30 min. A solution of potassium t-butoxide (1.91 g) in methanol (40 ml) was added to a solution of 4-nitro-2-oxo-5-pyridylpiperidine (3.01 g, Example 26a) in methanol (65 ml) and the mixture was stirred for 15 min. This solution was then added dropwise to the titanium trichloride/buffer solution at 0° C. under nitrogen. The reaction mixture was stirred at 0° C. for 15 min. Methanol was removed in vacuo and solid sodium hydroxide was added, with stirring and cooling, to the residual solution. The mixture was filtered and water was removed from the filtrate in vacuo. The residue was azeotroped with toluene and then redissolved in dichloromethane. Insoluble material was filtered off and the filtrate was concentrated in vacuo. The material was freeze-dried for 18 h to give 5-hydroxy-2-oxo-6-pyridylpiperidine as a mixture of cis and trans isomers. $^1$H NMR (250 MHz, CDCl$_3$) δ1.91–2.18 (2H, m, CH$_2$), 2.39–2.57 (1H, m, CH$\underline{H}$), 2.60–2.84 (1H, m, CH$\underline{H}$), 4.02–4.11 (0.4H, CHOH, trans isomer), 4.37–4.44 (0.6H, m, CHOH, cis isomer), 4.61 (0.4H, brd, NCH, trans isomer), 4.69 (0.6H, brd, NCH, cis isomer), 7.30–7.50 (2H, m, ArH), 7.77–7.88 (1H, m, ArH), 8.54–8.64 (1H, m, ArH).

c) 5-Hydroxy-2-oxo-6-pyridylpiperidine (2.19 g, Example 26b) was dissolved in tetrahydrofuran (50 ml) at room temperature under nitrogen. Borane-tetrahydrofuran complex (1.0M solution) (79.8 ml) was added and the reaction mixture was refluxed for 23 h. The reaction was allowed to cool and was quenched carefully with methanol before removing the solvent in vacuo. 6N Hydrochloric acid (50 ml) was added and the mixture was stirred for 45 min. The solvent was removed in vacuo and the residue was redissolved in methanol-water. The solution was basified with solid sodium hydroxide. Di-t-butyl-dicarbonate (4.23 g) was added and the reaction mixture was stirred for 18 h. Methanol was removed in vacuo and the product was extracted into ethyl acetate. The organic phase was dried (MgSO$_4$) and concentrated. The material was purified by chromatography on silica using 50% ethyl acetate in petroleum ether (60–80) as eluant to give cis-1-t-butyloxy-carbonyl-3-hydroxy-2-pyridylpiperidine. $^1$H NMR (250 MHz, CDCl$_3$) δ1.35–1.52 (9H, CH$_3$), 1.60–1.84 (3H, m, CH$_2$C$\underline{H}$H), 1.86–2.08 (1H, m, CH$\underline{H}$), 2.87–3.01 (1H, m, NC$\underline{H}$H), 3.99–4.13 (1H, m, NCH$\underline{H}$), 4.69–4.77 (1H, m, C$\underline{H}$OH), 5.24–5.31 (1H, br d, NC$\underline{H}$), 7.13–7.22 (2H, m, ArH), 7.63–7.73 (1H, m, ArH), 8.52–8.60 (1H, m, ArH).

d) cis-1-t-Butyloxycarbonyl-3-((3,5-bis(trifluoromethyl)phenyl)methyloxy)-2-pyridylpiperidine was prepared from cis-1-t-butyloxycarbonyl-3-hydroxy-2-pyridylpiperidine (375 mg, Example 26c) and 3,5-bis(trifluoromethyl)benzyl bromide (0.37 ml) in an analogous manner to that described in Example 2d. The material was purified by chromatography on silica using 10% then 20% ethyl acetate in petroleum ether (60–80) as eluant. MS (CI$^+$)m/z 504 (MH. 100%).

e) cis-1-t-Butyloxycarbonyl-3-((3,5-bis(trifluoromethyl)phenyl)methyloxy)-2-pyridylpiperidine (210 mg, Example 26d) was dissolved in methanol (5 ml) with stirring. A saturated solution of acetyl chloride in methanol was added and the mixture stirred for 2.5 h. Solvent was removed in vacuo and the material was recrystallised from diethyl ether-methanol to provide the title compound as a white crystalline solid. $^1$H NMR (360 MHz, DMSO) δ1.56–1.69 (1H, m, CHH), 1.81–2.02 (2H, m, CH$_2$), 2.38–2.47 (1H, m, CHH), 2.97–3.10 (1H, m, NCHH), 3.24 (1H, brd, NCHH), 3.74–3.84 (1H, m, CHO), 4.29–4.48 (2H, m, NCH and OCHH), 4.72 (1H; d, J=13.1 Hz, OCHH), 7.43–7.50 (1H, m, ArH), 7.56 (3H, brs, ArH), 7.83–7.89 (1H, m, ArH), 7.94 (1H, s, ArH), 8.57–8.62 (1H, m, ArH); MS (CI$^+$) m/z 404, (MH, 100%).

EXAMPLE 27:
cis-3-((3,5-Bis(trifluoromethyl)phenyl)methyloxy)-6-keto-1-(4-methoxybenzyl)-2-phenyl a) cis-3-(t-Butyldimethylsilyloxy)-6-keto-2-phenyl piperidine Sodium borohydride (2 g) was added to a cooled (–10° C.) suspension of 3,6-diketo-2-phenylpiperidine (20 g, Example 2b) in methanol (300 ml) with stirring. After 0.5 h the solvent was removed in vacuo, and the residue dissolved in water (100 ml), then neutralised (pH 7, acetic acid) and extracted with ethyl acetate (3×100 ml). The combined organic phases were dried (K$_2$CO$_3$) and concentrated to leave a white solid. A further batch was obtained by continuous extraction of the aqueous layer with ethyl acetate.

This material was suspended in dichloromethane (200 ml), cooled to 0° C. and 2,6-lutidine (13 ml) was added followed by t-butyldimethylsilyl trifluoromethanesulfonate (25.5 ml). The resultant pale yellow solution was stirred at 23° C. for 5 h, then poured into saturated aqueous sodium bicarbonate solution (200 ml), the layers were separated and the aqueous phase extracted with dichloromethane (3×100 ml). The combined organic phases were dried (K$_2$CO$_3$) and concentrated and the residue triturated with hexanes to leave the product as a white solid, m.p.=139°–142° C.

b) cis-3-(t-Butyldimethylsilyloxy)-6-keto-1-(4-methoxybenzyl)-2-phenyl piperidine. The product of part a) (2 g) was dissolved in N,N-dimethylformamide (15 ml) with stirring and sodium hydride (80% in oil; 0.236 g) was added. After 0.5 h 4-methoxybenzylchloride (1.1 ml) was added and the mixture stirred at 23° C. for 16 h, then diluted with water (150ml) and extracted with ethyl acetate (3×80 ml). The combined organic phases were washed with brine (1×50 ml) then dried (MgSO$_4$) and concentrated to leave an oil. Purification on silica gel eluting with hexanes/ethyl acetate (4:1 then 1:1 then ethyl acetate) provided the product as an oil. $^1$H NMR (250 MHz, CDCl$_3$) δ7.36 (3H, m), 7.18 (2H, m), 7.04 (2H, d, J=8.4 Hz), 6.84 (2H, d, J=8.4 Hz), 5.52 (1H, d, J=14 Hz), 4.31 (1H, d, J=4.2 Hz), 4.02 (1H, m), 3.82 (3H, s), 3.32 (1H, d, J=14 Hz), 2.82 (1H, ddd, J=5.5, 10.7, 18.2 Hz), 2.54 (1H, m), 1.75 (2H, m), 0.78 (9H, s), –0.12 (3H, s), –0.28 (3H, s).

c) cis-3-Hydroxy-6-keto-1-(4-methoxybenzyl)-2-phenylpiperidine. The product of part b) (1.6 g) was dissolved in tetrahydrofuran (10 ml) and tetrabutylammonium fluoride (1M in tetrahydrofuran, 4.5 ml) was added. After 3 h saturated aqueous sodium hydrogen carbonate (10 ml) was added and the mixture was extracted with ethyl acetate (3×15 ml). The combined organic extracts were washed with brine (1×10 ml) then dried (MgSO$_4$) and concentrated to leave an oil. Purification on silica gel (hexanes/ethyl acetate 1:1 then ethyl acetate then methanol/ethyl acetate 1:9) provided the product as a white solid. $^1$H NMR (360 MHz, CDCl$_3$) δ7.39 (3H, m), 7.21 (2H, dd, J=1.8, 8.0 Hz), 7.05 (2H, d, J=8.6 Hz), 6.83 (2H, d, J=8.6 Hz), 5.50 (1H, d, J=14.5 Hz), 4.48 (d, J=5.3 Hz), 4.04 (1H, m), 3.79 (3H, s), 3.29 (1H, d, J=14.5 Hz), 2.78 (1H, ddd, J=5.5, 10.7, 18.2 Hz), 2.60 (1H, m), 1.60 (2H, m); m/z (CI$^+$) 312 (MH).

d) cis-3-((3,5-Bis(trifluoromethyl)phenyl)methyloxy)-6-keto1-(4-methoxybenzyl)-2-phenyl piperidine. The product of part c) (0.43 g) was alkylated with 3,5-bis(trifluoromethyl)benzyl bromide (0.38 ml) in an analogous manner to that described in Example 2d, to give the title compound as an oil. Analysis: Found: C, 62.58; H, 4.86; N, 2.74. C$_{28}$H$_{25}$NO$_3$F$_6$ requires C, 62.57; H, 4.69; N, 2.61%; m/z (CI$^+$) 538 (MH).

EXAMPLE 28:
cis-3-((3,5-Bis(trifluoromethyl)phenyl)methyloxy)-6-keto-2-phenyl piperidine cis-3-((3,5-Bis(trifluoromethyl)phenyl)methyloxy)-6-keto-1-(4-methoxybenzyl)-2-phenyl piperidine (0.17 g, Example 27) was dissolved in acetonitrile (3 ml) and water (1 ml) then cooled to 0° C. and cerium ammonium nitrate (173 mg) was added. The mixture was stirred at 23° C. for 18h, then poured into water (10 ml) and extracted with ethyl acetate (3×15 ml). The combined organic extracts were washed with brine (1×10 ml) then dried (MgSO$_4$) and concentrated to leave a pale yellow oil. Purification on silica gel (hexanes/ethyl acetate 1:1 then ethyl acetate then methanol/ethyl acetate 1:9) provided cis-3-((3,5-bis(trifluoromethyl)phenyl)methyloxy)- 6-keto-2-phenyl piperidine as an oil. $^1$H NMR (360 MHz, CDCl$_3$) δ7.72 (1H, s), 7.44 (2H, s), 7.37 (5H, m), 5.86 (1H, s), 4.75 (1H, d, J=3.2 Hz), 4.52 (1H, d, J=12.5 Hz), 4.14 (1H, d, J=12.5 Hz), 3.98 (1H, m), 2.65 (1H, ddd, J=6.4, 12.2, 18.2 Hz), 2.48 (1H, m), 2.30 (1H, m), 2.06 (1H, m). m/z (CI$^+$) 418 (MH).

EXAMPLE 29:
cis-3-((3,5-Bis(trifluoromethyl)phenyl)methyloxy)-1-(2-carbomethoxy)ethyl- 2-phenylpiperidine A solution of cis-3-((3,5-bis(trifluoromethyl)phenyl)methyloxy)-2-phenylpiperidine (1.3 g, Example 4, free base) in methyl acrylate (30 ml) was refluxed for 16 h. The solvent was removed in vacuo and the residue purified on silica gel (ethyl acetate-petrol (b.p. 60°–80° C.), 1:1) to provide title compound as an oil. m/z (CI$^+$) 490 (MH). $^1$H NMR (360 MHz, CDCl$_3$) δ7.70 (1H, s), 7.47 (2H, s), 7.40–7.26 (5H, m), 4.44 (1H, d, J=12.24 Hz, OCHHPh), 4.00 (1H, J=12.24 Hz, OCHHPh), 3.57 (3H, s), 3.53 (1H, bs), 3.31 (1H, s), 3.17 (1H, bd), 2.96–2.89 (1H, m), 2.48–2.37 (3H, m), 2.27–2.0 (3H, m), 1.62–1.51 (3H, m). Found: C, 58.62; H, 5.20; N, 2.74. C$_{24}$H$_{25}$F$_6$NO$_3$ requires C, 58.90; H, 5.15; N, 2.86%.

EXAMPLE 30:
cis-3-((3,5-Bis(trifluoromethyl)phenyl)methyloxy)-1-(carboxamido)ethyl)-2-phenylpiperidine A solution of the product of Example 29, (0.5 g) in methanol (40 ml) was saturated with ammonia at –30° C., sealed and stored at 25° C. for 72 h. The solution was evaporated to dryness and the residue chromatographed on silica gel eluting with ethyl acetate. The eluted product was concentrated and recrystallised from ethyl acetate to give the title compound, m.p.=72°–80° C.; m/z (CI$^+$) 475 (ME); Found: C, 58.51; H, 5.17; N, 5.63. C$_{23}$H$_{24}$F$_6$N$_2$O$_2$ requires C, 58.23; H, 5.10; N, 5.91%.

EXAMPLE 31:
cis-3-((3,5Bis(trifluoromethyl)phenyl)methyloxy)-1-(3-carbomethoxy)propyl- 2-phenylpiperidine A solution of the product of Example 4, (4 g), methyl-4-bromobutyrate (2.4 g) and potassium carbonate (3.8 g) in dry dimethylformamide (20 ml) was heated at 110° C. for 16 h. To the cooled solution was added ethyl acetate and water and the organic phase washed further with water and dried (MgSO$_4$). After the solvent had been removed in vacuo the residue was chromatographed on silica gel eluting with ethyl acetate/petrol (60°–80° C.) (1:9) to give the title compound, m.p.=60°–70° C. m/z (CI$^+$) 504 (MH). Found: C, 59.65; H, 5.44; N, 2.81. C$_{25}$H$_{27}$F$_6$NO$_3$ requires C, 59.64; H, 5.41: N, 2.78%.

EXAMPLE 32:
cis-3-((3,5Bis(trifluoromethyl)phenyl)methyloxy)-1-(3-carboxamido)propyl-2-phenylpiperidine The title compound was prepared from the product of Example 31 using a procedure analogous to that described in Example 30 and obtained as an oil, m/z (CI$^+$) 489 (MH). Found: C, 58.89; H, 5.64; N, 5.75. C$_{24}$H$_{26}$F$_6$N$_2$O$_2$ requires C, 59.01; H, 5.37; N, 5.74%.

EXAMPLE 33:
(2S,3S)-1-t-Butoxycarbonyl-3-((3-methyl-5 (trimethylsilyl)phenyl)methyloxy-2-phenylpiperidine a) 3-Methyl-5-(trimethylsilyl)benzyl bromide 5-Bromo-m-xylene (12 g) was added dropwise to a mixture of magnesium turnings (2.3 g) and iodine (1 crystal) in tetrahydrofuran (150 ml) under a nitrogen atmosphere. The mixture was heated at reflux for 2H, then cooled. Freshly distilled trimethylsilyl chloride (16.4 ml) was added to the mixture dropwise and the resulting mixture was stirred for 30 min. The solvent was removed in vacuo. The residue was washed with ammonium chloride solution, extracted with ether (2×100 ml) and dried (MgSO$_4$). The ether was removed in vacuo to afford a brown oil. This oil (7.1 g) was dissolved in carbon tetrachloride (40 ml) under a nitrogen atmosphere. N-Bromosuccinimide (7.1 g) and azobisisobutyronitrile (10 mg) were added to the solution and the mixture was heated at 60° C. for 2 h. The solvent was removed in vacuo and the residue was purified by chromatography on silica using hexane as eluant. This afforded 3-methyl-5-(trimethylsilyl)benzyl bromide as a brown oil. $^1$H NMR (360 MHz, CDCl$_3$) δ0.26 (9H, s, Si(CH$_3$)3), 2.35 (3H, s, CH$_3$), 4.47 (2H, s, CH$_2$Br), 7.20 (1H, s, ArH), 7.24 (1H, s, ArH), 7.30 (1H, s, ArH).

b) (+)-cis-3-Hydroxy-2-phenylpiperidine (Example 5c) was treated analogously to that described in Example 2e and then alkylated as described in Example 2d using 3-methyl-5-(trimethylsilyl)benzyl bromide to give the title compound as a colourless oil. $^1$H NMR (360 MHz, CDCl$_3$) δ0.24 (9H, s, SICCH3)$_3$), 1.46 (9H, s, NCOOC(CH$_3$)$_3$), 1.54–1.74 (2H, m, CH$\overline{2}$), 1.85–2.00 (2H, m, CH$_2$), 2.34 (3H, s, ARCH$_3$), 2.65–2.76 (1H, m, NCHH), 3.77–3.87 (1H, m, NCH$\overline{H}$), 3.88–3.96 (1H, bd, CH$\overline{O}$), 4.56 (1H, d, J=11.5 Hz, $\overline{O}$C HHAr), 4.67 (1H, d, J=11.5 Hz, OCHHAr), 5.73 (1H, bs, N $\overline{H}$Ph), 7.10 (1H, s, ArH), 7.22–7.37 (5, m, ArH), 7.60–7.62 (2H, 2s, Ar—H); MS (CI$^+$) 454 (MH, 75%); Found: C, 71.75; H, 8.62; N, 3.25. C$_{27}$H$_{39}$NO$_3$Si requires C, 71.48; H, 8.66; N, 3.09.

EXAMPLE 34:
cis-2-Phenyl-3-(phenylmethyloxy)piperidine oxalate salt cis-1-t-Butyloxycarbonyl-3-hydroxy-2-phenylpiperidine (Example 2c, 1 g) was dissolved in dry dimethylformamide (10 ml). Sodium hydride (163 mg, 80% dispersion in oil) was added and the mixture was stirred for 30 minutes at room temperature. Benzyl bromide (923 mg) was added and the mixture was stirred for 3 h. Excess sodium hydride was destroyed (ammonium chloride), the mixture was diluted with water and extracted with ethyl acetate (2×30 ml). The organic washings were washed with brine, dried (MgSO$_4$) and evaporated. The crude residue was purified by chromatography on silica using petrol/ether (70:30) as eluant. The product was dissolved in ether and the solution cooled to 0° C. Anhydrous hydrogen chloride was bubbled through the solution for 30 min. The ether was then evaporated and the crude product was dispersed between ethyl acetate and aqueous potassium carbonate. The organic extract was dried (MgSO$_4$) and evaporated and the crude oil was purified by chromatography on silica using 7% methanol in dichloromethane as eluant. The product was dissolved in ethereal oxalic acid and recrystallised from ethyl acetate-ether, m.p. 150°–151° C. $^1$H NMR (360 MHz, CDCl$_3$, free base) δ1.58–1.72 (2H, m, NCH$_2$CH$_2$CH$_2$), 2.04–2.17 (2H, m, NCH$_2$CH$_2$), 2.94–3.02 (1H, m, CH$\overline{H}$HN), 3.36–3.39 (1H, m, —CH$\overline{H}$N), 3.72 (1H, s, NCHC$\overline{H}$O), 4.11 (1H, s, NC HCH$\overline{O}$), 4.19 (1H, d, J=12.0 Hz, $\overline{O}$CHHPh), 4.35 (1H, d, J=12.0 Hz, OCHHPh), 7.00–7.03 (2H, m, ArH), 7.18–7.21 (3H, m, ArH), 7.31–7.35 (3H, m, ArH), 7.39–7.41 (2H, m. ArH), 7.67 (1H, s, NH); MS (FAB) m/z 267 (MH, 25%). Found: C, 66.86; H, 6.44; N, 3.97. Calcd. for C$_{18}$H$_{21}$NO.(COOH)$_2$.0.25H$_2$O requires C, 66.56; H, 6.28; N, 3.88%.

EXAMPLE 35:
cis-3-((3,5.-Di-t-butylphenyl)methyloxy)-2-phenylpiperidine oxalate salt a) 3,5-Di-t-butylbenzyl bromide
3,5-Di-t-butyltoluene (5 g), N-bromosuccinimide (4.79 g) and azobisisobutyronitrile (20 mg) were dissolved in carbon tetrachloride (30 ml) and the solution was heated at reflux for 3 h. When cool, a white solid was removed by filtration, and the filtrate was concentrated yielding a yellow oil, which was used without further purification. $^1$H NMR (360 MHz, CDCl$_3$) δ1.30 (18H, s, CH$_3$), 4.45 (2H, s, CH$_2$), 7.2 (2H, d, J=1.75 Hz, ArH), 7.4 (1H, s, ArH).

b) cis-3-((3,5-Di-(t-butyl)phenyl)methyloxy)-2-phenylpiperidine oxalate salt

This was prepared from cis-1-t-butyloxycarbonyl-3-hydroxy-2-phenylpiperidine (Example 2c) and 3,5-di-t-butylbenzylbromide following the procedure described in Example 2d, e. m.p.=205°–207° C. $^1$H NMR (360 MHz, CDCl$_3$ free base) δ1.25 (18H, s, CH$_3$), 1.33–1.64 (2H, m, CH$_2$CH$_2$), 1.92–2.04 (1H, m, CHH), 2.18–2.21 (1H, m, C HH), 2.81–2.89 (1H, m, CHHN), 3.28–3.31 (1H, m, CH HN), 3.72 (1H, s, CHO), 3.88 (1H, s, NCHPh), 4.20 (1H, d, J=12.0 Hz, OCHH), 4.34 (d, J=12.0 Hz, OCH$\underline{H}$), 6.92 (2H, d, J=1.8 Hz, Ar$\overline{H}$), 7.13–7.38 (4H, m, ArH), 7.43–7.45 (2H, m, ArH); MS (CI$^+$) m/z, 380 (MH. 100%). Found: C, 71.37; H, 8.43; N, 3.07. C$_{26}$H$_{36}$NO.(COOH)$_2$ requires C, 71.61; H, 8.37; N, 2.98%.

EXAMPLE 36:
(2S,3S)-3-((3-Methyl-5-iodo)phenyl)methyloxy)-2-phenylpiperidine hydrochloride (2S,3S)-1-t-Butoxycarbonyl-3-((3-methyl-5-(trimethylsilyl)phenyl)methyloxy)-2-phenylpiperidine (Example 33. 462 mg) was dissolved in dry methanol (5 ml) and stirred under nitrogen. The solution was cooled to 0° C. and silver trifluoroacetate (500 mg) was added. After 5 minutes iodine (259 mg) was added which resulted in precipitation of a yellow solid; this was allowed to stir overnight. Methanol was removed in vacuo affording a yellow solid which was suspended in ethyl acetate (10 ml) and filtered through celite to remove inorganic matter. The ethyl acetate solution was washed with sodium sulphite (2×5 ml), brine (1×5 ml), dried (MgSO$_4$) and concentrated in vacuo to afford a clear oil. This was purified on silica using 5% ethyl acetate in hexane as eluant. After evaporation of the solvent, the product was then cooled in an ice bath while trifluoroacetic acid (5 ml) was added dropwise: the resulting solution was stirred for 30 min. Excess trifluoroacetic acid was removed in vacuo and the residue was partitioned between dichloromethane and aqueous sodium hydroxide solution. The aqueous layer was washed with dichloromethane (2×30 ml) and the combined organic layers were washed with brine, dried (MgSO$_4$) and evaporated to afford a yellow oil. This was dissolved in methanolic hydrogen chloride and evaporated. The resulting solid was recrystallised from ethyl acetate-methanol, m.p.= 207°–209° C. $^1$H NMR (360 MHz, CDCl$_3$, free base) δ1.4–2.0 (4H, m, NCH$_2$CH$_2$CH$_2$), 2.15 (3H, s, CH$_3$), 2.18 (1H, m, NH), 2.78–2.86 (1H, m, NCHH), 3.24–3.29 (1H, m, NCHH), 3.60 (1H, s, CHO), 3.79 (1H, s, NCHPh), 4.01 (1H, d, J= 9.5 Hz, OCHHAr), 4.29 (1H, d, J=9.5 Hz, OCH HArH), 6.65 (1H, s, ArH), 7.12 (1H, s, ArH), 7.24–7.36 (6H, m, ArH); Found: C, 51.66; H, 5.27; N, 3.12. C$_{19}$H$_{22}$NOI.HCl requires C, 51.43; H, 5.22; N, 3.15%.

EXAMPLE 37:
cis-3-(3,5-Bis(trifluoromethyl)phenyl)methyloxy)-1-carbomethoxyformyl-2-phenyl piperidine cis-3-((3,5-Bis(trifluoromethyl)phenyl)methyloxy)-2-phenyl piperidine hydrochloride salt (0.5 g, Example 4) was suspended in dichloromethane (3 ml) and triethylamine (0.477 ml) was added followed by methyl oxalyl chloride (0.115 ml). The reaction mixture was stirred at 23° C. for 4 h, then poured into saturated aqueous sodium bicarbonate solution (5 ml) and extracted with dichloromethane (3×20 ml). The combined organic phases were dried (MgSO$_4$) and concentrated to leave an oil. Purification on silica gel (hexanes/ethyl acetate 3:1) provided the title compound as an oil. m/z (CI$^+$) 490 (MH).

EXAMPLE 38:
cis-3-(3,5-Bis(trifluoromethyl)phenyl)methyloxy)-1-carboxamidoformyl-2-phenyl piperidine The title compound was prepared from cis-3-(3,5-bis(trifluoromethyl)phenyl)methyloxy)-1-carbomethoxyformyl-2-phenylpiperidine (Example 37) by a procedure analogous to that described in Example 7, m.p.=78°–81° C. Analysis: Found: C, 55.05; H, 4.39; N, 5.95. C$_{22}$H$_{22}$N$_2$O$_3$F$_6$.[0.5 CH$_3$OH] requires C, 55.11; H, 4.52; N, 5.71%.

EXAMPLE 39:
cis-N-(1-Acetamidooxime)-3-(3,5-bis(trifluoromethyl)phenyl)methyloxy)-2-phenylpiperidine The compound of Example 4 (800 mg), hydroxylamine hydrochloride (188 mg) and potassium carbonate (500 mg) were suspended in ethanol (10 ml) and the contents were heated at reflux for 5 h. The mixture was cooled and evaporated and the residue was partitioned between dichloromethane and brine. The organic layer was dried (MgSO$_4$) and concentrated in vacuo. The resulting white solid was recrystallised from ethyl acetate and petrol, m.p. 178°–179° C. $^1$H NMR (360 MHz, CDCl$_3$) δ1.55 (2H, m,NCH$_2$CH$_2$C H$_2$), 1.95–2.1 (3H, m, NCHHCH$_2$CH$_2$), 2.35 (1H, d, J=14.0 Hz, NCHH), 3.1 (1H, d, J=14.0 Hz, NCHHCH$_2$CH$_2$), 3.32 (1H, d, J=14.0 Hz, NCHH), 3.34 (1H, s, CHO), 3.55 (1H, s, CHN), 4.02 (1H, d, J=12.0 Hz, OCHH), 4.45 (1H, d, J=12.0 Hz, OCHH), 5.07 (2H, s, NH$_2$), 7.2–7.3 (4H, m, ArH+ NOH), 7.55–7.4 (2H, d, J=6.0 Hz, ArH), 7.5 (2H, s, ArH), 7.70 (1H, s, ArH). MS (CI$^+$) m/z 476 (MH). Found: C, 55.4; H, 4.92; N, 8.94. Calcd. for C$_{22}$H$_{23}$N$_3$O$_2$F$_6$: C, 55.58; H, 4.88; N, 8.84.

EXAMPLE 40: cis-3
((3,5Bis(trifluoromethyl)phenyl)methyloxy)-1-cyanomethyl-2-phenylpiperidinium hydrochloride The compound of Example 4 (5 g), potassium carbonate (1.7 g) and bromoacetonitrile (0.87 ml) were suspended in dimethylformamide (15 ml) and the mixture was stirred under nitrogen at 60° C. for 3 h. The mixture was cooled, diluted with water (200 ml) and extracted with ethyl acetate (2×50 ml). The organic extracts were washed with brine, dried (MgSO$_4$) and evaporated, affording a brown oil. This was purified on silica gel using ethyl acetate in petrol (10%) as eluant. This afforded the product as a colourless oil. The hydrochloride salt was prepared by dissolution in ethereal hydrogen chloride and the salt was recrystallised from diethyl ether-hexane, m.p. 133°–134° C. $^1$H NMR (360 MHz, CDCl$_3$) δ1.75 (2H, m, CHH), 1.90 (2H, m, CHH), 2.31 (1H, mc, CHH), 2.71 (1H, m, CHH), 3.19 (1H, m, CH HN), 3.72 (1H, m, CHHN), 3.81 (1H, d, J=17.5 Hz, NC HHCN), 3.86 (1H, s, CHO), 4.02 (1H, d, J=17.5 Hz, NCH HCN), 4.09 (1H, s, CHPh), 4.35 (1H, d, J=3.0 Hz, OC HH), 4.73 (1H, d, J=13.0 Hz, OCHH), 7.4 (3H, m, ArH), 7.69–7.73 (5H, m, ArH); MS (CI$^+$) m/z 443 (MH, 30%). Found: C, 54.87; H, 4.30; N, 5.66. Calcd. for C$_{22}$H$_{18}$F$_6$N$_2$O.HCl: C, 55.18; H, 4.42; N, 5.85%.

EXAMPLE 41:
(+)-cis-3-((3,5Bis(trifluoromethyl)phenyl)methyloxy)-1-carboxymethyl-2-phenyl piperidine The methyl ester (1.8 g; Example 8) was dissolved in tetrahydrofuran (25 ml) and a solution of potassium hydroxide (0.6 g) in water (25 ml) was added. The reaction mixture was heated at reflux for 18 H, then the organic layer was removed in vacuo and the aqueous layer removed by freeze-drying. The residue was dissolved in the minimum volume of water and the pH adjusted to 7.0 by the addition of 2M hydrochloric acid. The precipitated solid was isolated by filtration and washed with water and then recrystallised from ethanol, m.p.=60°–63° C. Found: C, 53.11; H, 4.54; N, 3.05. Calcd. for C$_{22}$H$_{21}$F$_6$NO$_3$.HCl C, 53.08; H, 4.45; N, 2.81%. m/z (CI$^+$) 462 (MH).

EXAMPLE 42:
cis-3-((3,5-Bis(trifluoromethyl)phenyl)methyloxy)-1-((3,5-bis(trifluoromethyl)phenyl)methyl-2-phenylpiperidine The title compound was prepared from cis-3-((3,5-bis(trifluoromethyl)phenyl)methyloxy)-2-phenylpiperidine (Example 4) and 3,5-bis-trifluoromethyl benzyl bromide in an analogous manner to that described in Example 17. Found: C, 53.91; H, 3.62; N, 2.08. Calcd. for C$_{29}$H$_{23}$F$_{12}$NO.0.3H$_2$O C, 53.74; H, 3.89; N, 2.16%.

EXAMPLE 43:
cis-3-((3,5-Bis(trifluoromethyl)phenyl)methyloxy-1-(N,N-diethylcarboxamido)methyl-2-phenyl piperidinium hydrochloride (+)-cis-3-((3,5-Bis(trifluoromethyl)phenyl)methyloxy)-1-carboxymethyl-2-phenyl piperidine (1 g, Example 41), 1-hydroxybenzotriazole hydrate (1.2 g), 1-(3-dimethylaminopropyl)3-ethyl-carbodiimide hydrochloride (1.66 g), triethylamine (1.2 ml) and diethylamine (0.55 ml) were added together and the reaction was left stirring overnight at room temperature. The solvent was removed in vacuo and the residual yellow oil dispersed between water and ethyl acetate. The organic layer was washed with 1M citric acid, water, sodium hydrogen carbonate, brine, dried (MgSO$_4$) and concentrated in vacuo to afford a yellow oil. This was purified on silica gel eluted with 50% ethyl acetate in petrol. The product was purified further by medium pressure chromatography eluting with 75% ethyl acetate in petrol to afford an oil. The hydrochloride salt was prepared (HCl, methanol) and crystallised from ethyl acetate-hexane, m.p.=135°–137° C. Found: C, 55.66; H, 5.85; N, 4.90. C$_{26}$H$_{30}$N$_2$O$_2$F$_6$ requires C, 56.02; H, 5.70; N, 5.03%.

EXAMPLE 44:
cis-3-((3-methyl-5-trimethylsilyl)benzyloxy)-2-phenyl piperidine The Boc-protected ether (0.087 g, Example 33) was dissolved in anhydrous dichloromethane (5 ml) and stirred under nitrogen. t-Butyldimethylsilyl trifluoromethane sulfonate (0.044 ml) was added and the reaction left overnight. The reaction mixture was washed with water, the organic layer was dried (MgSO$_4$) and concentrated in vacuo to give a clear oil. Purification was carried out on silica gel eluting with dichloromethane then 3% methanol in dichloromethane to afford a clear oil. $^1$H NMR (360 MHz, CDCl$_3$ free base) δ1.95 (9H, s, Si(CH$_3$)$_3$), 1.48–1.61 2H, m, CH$_2$), 1.92–2.18 (2H, m, CH$_2$), 2.23 (3H, s, ARCH$_3$), 2.78–2.86 (1H, m, NCHH), 3.20–3.27 (1H, m, NCHH), 3.67 (1H, s, CHO), 3.95 (1H, s, NCHPh), 4.18–4.21 (1H, d, J=12 Hz, OCHHAr), 4.35–4.39 (1H, d, J=12 Hz, OCHHAr), 6.79 (H, s, ArH), 6.98 (H, s, ArH), 7.16 (H, s, ArH), 7.30–7.38 (5H, m, ArH). MS (CI$^+$) m/z 354 (MH, 100%).

EXAMPLE 45:
cis-3-((2-Methoxy-5-nitrophenyl)methyloxy)-2-phenylpiperidine hydrochloride salt The Boc-protected alcohol (4.17 g, Example 2c) was dissolved in N,N-dimethylformamide (15 ml) under nitrogen, sodium hydride (0.43 g) was added carefully and the mixture stirred for 0.5 h. 2-Methoxy-5-nitro benzyl bromide (4.45 g) was added and the solution changed colour from black to brown. After 3 h the reaction was quenched with ammonium chloride. The product was extracted using ethyl acetate, dried and concentrated to afford a brown oil. This was purified on silica gel eluting with 5% ethyl acetate in hexane to provide an oil. This oil was dissolved in ether and then saturated with hydrogen chloride. The precipitated solid was isolated by filtration and recrystallised from ethyl acetate-methanol, m.p.=246°–248° C. $^1$H NMR (360 MHz, CDCl$_3$ free base) δ1.50–1.59 (1H, m, CHH), 1.64–1.75 (1H, m, CHH), 1.87–2.01 (1H, m, CHH), 2.22–2.32 (1H, m, C HH), 2.80–2.92 (1H, m, NCHH), 3.27–3.35 (1H, m, NC HH), 3.69 (1H, bs, CHO), 3.80 (3H, s, OCH$_3$), 3.86 (1H, bs, NCHPh), 4.09–4.13 (1H, d, J=13 Hz, OCHHPh), 4.50–4.54 (1H, d, J=13 Hz, OCHHPh), 6.76–6.78 (1H, d, J=9 Hz. Ar H), 7.20–7.40 (5H, m, ArH), 8.00–8.11 (2H, m, ArH). MS (CI$^+$) m/z 343 (MH, 45%). Found: C, 60.52; H, 5.96; N, 7.45. C$_{19}$H$_{22}$N$_2$O$_4$.HCl requires C, 60.24; H, 6.12; N, 7.39%.

EXAMPLE 46:
cis-3-((2-Methoxy-5-aminophenyl)methyloxy)-2-phenylpiperidine hydrochloride The 5-nitro compound (0.324 g, Example 45) was dissolved in methanol (20 ml) with 1ml of 2N HCl. A spatula of wetted Pd/C was added and the reaction placed under an atmosphere of hydrogen for 1 h at 23° C. The solvent was removed in vacuo and the residue basified (2M NaOH) and extracted with ethyl acetate. The combined organic extracts were dried (MgSO$_4$) and concentrated to leave a brown oil. Purification by column chromatography eluting with 8% methanol in dichloromethane provided an oil. The hydrochloride salt was prepared and recrystallised from ethyl acetate-methanol, m.p.=241°–243° C. $^1$H NMR (360 MHz, CDCl$_3$ free base) δ1.25–1.65 (2H, m, CH$_2$), 1.93–2.07 (1H, m, CHH), 2.23–2.31 (1H, m, CHH), 2.82–2.91 (1H, m, NC HH), 3.1–3.5 (3H, m, NH$_2$+NCHH), 3.64 (3H, s, OCH$_3$), 3.70 (1H, bs, CHO), 3.89 (1H, bs, NCHPh), 4.22–4.25 (1H, d, J=14 Hz), 4.46–4.50 (1H, d, J=14 Hz, OCHHAr), 6.29 (1H, bs, ArH), 6.44–6.49 (1H, m, ArH), 6.55–6.57 (1H, d, J=9 Hz, ArH), 7.25–7.38 (3H, m, ArH), 7.42–7.48 (2H, m, ArH).

EXAMPLE 47:
cis-3-((3,5-Dichlorophenyl)methyloxy)-2-phenylpiperidine hydrochloride salt The title compound was prepared from 1-t-butyloxycarbonyl-3-hydroxy-2-phenylpiperidine (Example 2c) and 3,5-dichlorobenzylbromide in an analogous manner to that described in Example 2d, e, m.p.=243°–245° C. $^1$H NMR (360 MHz, CDCl$_3$) 1.49–1.53 (1H, m, CHH), 1.60–1.70 (1H, m, CHH), 1.82–1.95 (1H, m, CHH), 2.14–2.18 (1H, m, CHH), 2.79–2.87 (1H, m, NCHH), 3.27–3.31 (1H, m, NCH H), 3.60 (1H, s, OCHCHN), 3.82 (1H, s, OCHCHN), 4.02–4.05 (1H, d, J=13 Hz, OCHH), 4.31–4.35 (1H, d, J=13 Hz, OCHH), 6.80 (2H, s, ArH), 7.15 (1H, s, ArH), 7.25–7.35 (5H, m, ArH). Found: C, 58.24; H, 5.38; N, 3.91. Calcd. for C$_{18}$H$_{19}$NOCl$_2$.HCl C, 58.01; H, 5.41; N, 3.76%.

EXAMPLE 48:
3-((3,5-Bis(trifluoromethyl)phenyl)methyloxy)-3-methyl-2-phenylpiperidine oxalate salt a) Oxalyl chloride (1 ml) was added dropwise to a solution of methyl sulphoxide (0.82 ml) in anhydrous dichloromethane (4 ml) at −78° C. under a nitrogen atmosphere. A solution of 1-t-butoxycarbonyl-3-hydroxy-2-phenyl piperidine (1.6 g, Example 2c) in anhydrous dichloromethane (10 ml) was added, and the reaction stirred for 1.75 h before triethylamine (4 ml) was added and the reaction allowed to warm to room temperature. The reaction was partitioned between ethyl acetate and water, the organic phase washed with brine, dried and evaporated in vacuo to provide 1-t-butoxycarbonyl-2-phenylpiperidin-3-one as an oil.

b) A solution of 1-t-butoxycarbonyl-2-phenyl-piperidin-3-one (0.57 g, Example 48a) in 5 ml anhydrous tetrahydrofuran at −78° C. was treated with methyl magnesium bromide (1.6 ml of 1.5M solution in toluene-THF). The reaction was partitioned between saturated ammonium chloride-diethyl ether, the organic phase dried and evaporated in vacuo. The residue was chromatographed using 20% ethyl acetate in hexane as eluant to give 1-t-butoxycarbonyl, 3-methyl-2-phenyl piperidin-3-ol as a crystalline solid, m.p.=95°–97° C.

c) 1-t-Butoxycarbonyl-3-methyl-2-phenylpiperidin-3-ol (Example 48b) was alkylated with 3,5-bis(trifluoromethyl)benzylbromide in a manner analogous to that described in Example 2d and then deprotected as described in Example 2e and the oxalate salt prepared and recrystallised from diethyl ether, m.p.=230°–232 ° C. $^1$H NMR (360 MHz, d$_6$-DMSO) δ1.05 (3H, s), 1.7–2.0 (3H, m), 2.3–2.4 (1H, m), 3.0–3.2 (1H, m), 3.3–3.4 (1H, m), 4.5 (1H, s), 4.6–4.8 (2H, m), 7.4–7.5 (3m), 7.5–7.6 (2H, m), 8.00 (1H, s), 8.1 (2H, s): Found: C, 53.04; H, 4.53; N, 2.64:$C_{21}H_{21}NOF_6.1.3\ C_2H_2O_4$ requires C, 53.04; H, 4.45; N, 2.64.

EXAMPLE 49:
cis-3-((3,5-Bis(trifluoromethyl)phenyl)methyloxy-1-(N-benzylcarboxamido)methyl-2-phenyl piperidinium hydrochloride The title compound was prepared from (+)-cis-3-((3,5-bis(trifluoromethyl)phenyl)methyloxy)-1-carboxymethyl-2-phenyl piperidine (Example 41) and benzylamine in an analogous manner to that described in Example 43, m.p.=184°–186° C. Found: C, 59.53; H, 5.05; N, 4.67. $C_{29}H_{28}N_2F_6.HCl$ requires C, 59.34; H, 4.98; N, 4.77%.

EXAMPLE 50:
cis-3-((3,5-Bis(trifluoromethyl)phenyl)methyloxy-1-(N-methylcarboxamido)methyl-2-phenyl piperidine The title compound was prepared from cis-3-((3,5bis(trifluoromethyl)phenyl)methyloxy)-1-(carbomethoxy)methyl-2-phenyl piperidine (Example 6) and methylamine in an analogous manner to that described in Example 7. The hydrochloride salt was recrystallised from diethyl ether-hexanes, m.p.=140°–145° C. Found: C, 51.41; H, 5.17; N, 5.24. Calcd. for $C_{23}H_{24}N_2O_2F_6.1.5H_2O$ C, 51.36; H, 5.25; N. 5.21%.

EXAMPLE 51:
cis-3-((3,5-Dimethylphenyl)methyloxy)-1-methyl-2-phenyl azetidine oxalate salt a) To a suspension of sodium hydride (2.4 g) in N,N-dimethylformamide (50 ml) at 0° C. was added a mixture of methyl glycolate (5 g) and 3,5-dimethyl benzyl bromide (11 g) dropwise. The reaction was then quenched after 5 hours with iso-propanol/methanol solution. The reaction mixture was poured onto iced water and extracted with ether. The organic phase was dried ($MgSO_4$), filtered and evaporated. The crude material was chromatographed on flash silica and eluted with ethyl acetate:petrol (1:9) to afford methyl-O-(3,5-dimethylbenzyl)glycolate as a solid.

b) To a solution of methyl-O-(3,5-dimethylbenzyl)glycolate (7.47 g) in methanol (100 ml) aqueous sodium hydroxide (18 ml) was added via pipette. Water was added dropwise until formation of a precipitate. The solvent was removed in vacuo and the aqueous layer acidified using 2N HCl, then extracted with ethyl acetate. The organic phase was drivel ($MgSO_4$), filtered and evaporated to afford 3.5-dimethyl benzyl glycolic acid. $^1$H NMR (360 MHz, $CDCl_3$) δ9.5 (1H, s, broad), 6.97 (1H. s), 6.95 (1H, s), 4.57 (2H, s), 4.12 (2H, s), 2.31 (6H, s).

c) 3,5-Dimethyl benzyl glycolic acid (5.59 g) was cooled to 0° C. Thionyl chloride (5 ml) was added and the stirred solution was refluxed for 2 h. The solvent was removed in vacuo to afford 3,5-dimethyl benzyl glycolic acid chloride as an oil.

d) To a solution of triethylamine (5.89 g) in dichloromethane (50 ml), N-benzylidenemethyl amine (3.09 g) was added via syringe. The solution was cooled to 0° C. and 3,5-dimethyl benzyl glycolic acid chloride (3.31 g) in dichloromethane was added dropwise. After the solution had been stirred for 1 h 5N HCl was added. The organic layer was washed with brine, dried, filtered and evaporated. The crude material was chromatographed on flash silica and eluted with ethyl acetate:petrol, 1:1 to afford 3-((3,5-dimethylphenyl)methyloxy)-1-methyl-4-phenyl azetidin-2-one. $^1$NMR (360 MHz, $CDCl_3$) δ7.41 (3H, m), 7.33 (2H, m), 6.84 (1H, s), 6.48 (1H, s), 4.89 (1H, d, J=4 Hz), 4.67 (1H, d, J=4 Hz), 4.22 (1H, d, J=11 Hz), 4.08 (1H, d, J=11 Hz), 2.79 (1H, s), 2.20 (1H, s).

e) To a solution of aluminium chloride (0.29 g) in tetrahydrofuran (10 ml), lithium aluminium hydride (2.2 ml) was carefully added dropwise. After the reaction mixture had been stirred for 1 h, a solution of 3-((3,5-dimethylphenyl)methyloxy)-1-methyl-4-phenyl azetidin-2-one (0.66 g) in tetrahydrofuran (5 ml) was added via syringe. After a further hour water (1 ml) was carefully added dropwise followed by dropwise addition of 2N sodium hydroxide (1 ml). Dichloromethane (75 ml) was added followed by magnesium sulphate. After stirring for 30 minutes the solution was filtered. The organic phase was dried ($MgSO_4$), filtered and evaporated. The crude material was chromatographed on flash silica and eluted with ethyl acetate:petrol 1:1. The resulting compound was dissolved in ether and an ethereal solution of oxalic acid was added dropwise to give the title compound as a white solid, m.p.=147°–149° C. $^1$H NMR (360 MHz, DMSO) δ7.57 (2H, m), 7.43 (3H, m), 6.86 (1H, s), 6.62 (1H, s), 5.02 (m), 4.55 (m), 4.17 (1H, d, J=11 Hz), 3.94 (1H, d. J=11 Hz), 3.83 (1H, s), 2.61 (1H, s), 2.19 (1H, s); m/z ($CI^+$) 282 (MH). Found: C, 67.75; H, 7.00; N, 3.78. Calcd for $C_{19}H_{23}O_1N_1$. $[COOH]_2$: C, 67.91; H, 6.78; N, 3.77%.

EXAMPLE 52:
cis-3-((3-Bromophenyl)methyloxy)-2-phenylpiperidine hydrochloride salt The title compound was prepared from 1-t-butyloxycarbonyl-3-hydroxy-2-phenyl piperidine (Example 2c) and 3-bromobenzyl bromide in an analogous manner to that described in Example 2d. e, m.p. 215°–220° C.; m/z ($CI^{30}$) 346 (MH); Analysis: Found: C, 56.90; H, 5.56; N, 3.68. Calcd for $C_{18}H_{20}BrNO.HCl$; C, 56.49; H, 5.53; N, 3.66%.

EXAMPLE 53:
cis-3((3-cyanophenyl)methyloxy)-2-phenylpiperidine hydrochloride salt The title compound was prepared from 1-t-butyloxycarbonyl-3-hydroxy-2-phenyl piperidine (Example 2c) and α-bromo-m-tolunitrile in an analogous manner to that described in Example 2d, e, m.p. 168°–178° C.; m/z ($CI^+$) 293 (MH).

EXAMPLE 54:
cis-3-((3-Carboxyphenyl)methyloxy-2-phenylpiperidine cis-1-t-Butyloxycarbonyl-3-((3-cyanophenyl)methyloxy)-2-phenylpiperidine (prepared as an intermediate, Example 53, 3 g, 7.3 mmol) was refluxed in concentrated hydrochloric acid-methanol (1:1) for 16 h. The mixture was cooled and adjusted to pH 7 with sodium hydroxide, and the product extracted into ethyl acetate. The organic phase was washed ($H_2O$), dried ($MgSO_4$) and the solvent removed in vacuo. The residue was triturated with ether to give a white solid. m/z ($CI^+$) 326 (MH).

EXAMPLE 55:
cis-3-((3,5-Bis(trifluoromethyl)phenyl)methyloxy-6-hydroxymethyl-2-phenyl piperidine Mercuric acetate (4.92 g) was added to a solution of N-Boc-2-((3,5-bis(trifluoromethyl)phenyl)methyloxy)-1-phenyl-hex-5-enyl-1-amine (4 g, Example 20) in tetrahydrofuran (80ml) at 50° C. and the mixture stirred at this temperature for 16 h. The solvent was removed in vacuo and the residue dissolved in chloroform and mixed thoroughly with saturated potassium chloride solution. The layers were separated, and the aqueous phase extracted with chloroform (1×50 ml). The combined organic phases were dried (MgSO$_4$) and concentrated to leave a pale-yellow solid.

This material was dissolved in N,N-dimethylformamide (28 ml) and added dropwise during 15 min to a saturated solution of oxygen in N,N-dimethylformamide (24 ml) with continuous infusion of oxygen. The reaction mixture was stirred at 23° C. for 1 h, then diluted with diethyl ether (300 ml) and filtered through a pad of Celite. The filtrate was diluted with water (300 ml) and extracted with ethyl acetate (3×150 ml). The combined organic phases were washed with water (1×150 ml) and brine (1×150 ml) then dried (MgSO$_4$) and concentrated to leave an oil. Purification on silica gel eluting with hexanes-ethyl acetate (9:1 then 4:1 then 1:1) provided a clear oil. This material was dissolved in trifluoroacetic acid (10 ml) and allowed to stand at 23° C. for 10 min. The trifluoroacetic acid was removed in vacuo and the residue dissolved in dichloromethane (30 ml) and washed with 2M sodium hydroxide solution (2×10 ml), brine (1×10 ml) then dried (MgSO$_4$) and concentrated to leave an oil. Purification on silica gel eluting with hexanes-ethyl acetate (1% triethylamine: 4:1 then 3:1 then 1:1) then ethyl acetate provided the title compound as an oil. m/z (CI$^+$) 434 (MH).

EXAMPLE 56:
(2S,3S)-3-((3,5-Bis(trifluoromethyl)phenyl)methyloxy-1-((N-t-butyl)carboxamidomethyl)-2-phenylpiperidinium hydrochloride The compound of Example 41 was reacted with t-butylamine according to the procedure described in Example 43 to afford the title compound, m.p. 74°–76° C. $^1$H NMR (360 MHz, DMSO-d$_6$, free base) δ1.22 (9H, s, C(CH$_3$)$_3$), 1.52–1.55 (2H, m, CH$_2$), 1.87–1.91 (1H, m, CHH), 2.16–2.19 (1H, m, CHH), 2.32–2.35 (1H, m, NCHH), 2.38 (1H, d, J=16.0 Hz, NCHHC=O), 2.75 (1H, d, J=16.0 Hz, NCHHC=O), 2.89–2.92 (1H, m, NCHH), 3.59 (1H, s, NCHCHO), 3.63 (1H, s, NCHHO), 4.10 (1H, d, J=13.0 Hz, OCHH), 4.68 (1H, d, J=13.0 Hz, OCHH), 7.24–7.28 (3H, m, ArH), 7.40–7.46 (2H, m, ArH), 7.82 (2H, s, ArH), 7.96 (1H, s, ArH): MS (CI$^+$) m/z 516 ((MH), 100%).

EXAMPLE 57:
(2S,3S)-3-((3,5-Bis(trifluoromethyl)phenyl)methyloxy-1-((N-cyclopropyl)-2-phenylpiperidinium hydrochloride The compound of Example 41 was reacted with cyclopropylamine according to the procedure described in Example 43 to afford the title compound. $^1$H NMR (360 MHz, CDCl$_3$) δ0.49 (2H, m, CH$_2$-cyclopropyl), 0.80 (2H, m, CH$_2$-cyclopropyl), 1.50–1.68 (2H, m, CH$_2$), 2.04–2.27 (3H, m, CH$_2$+NCH), 2.50 (1H, br d, NCHHC=O), 2.70 (2H, m, CH-cyclopropyl), 3.00 (1H, m, NCHH), 3.14 (1H, br d, NCHHC=O), 3.43 (1H, brs, CHO), 3.58 (1H, brs, NC HPh), 4.03 (1H, d, J=12.0 Hz, OCHH), 4.48 (1H, d, J=12.0 Hz, OCHH), 7.26–7.30 (6H, m.ArH+NH), 7.56 (2H, s, ArH), 7.75 (1H, s, ArH). MS (CI$^+$) m/z 501 (MH).

The following examples illustrate pharmaceutical compositions according to the invention.

EXAMPLE 58A Tablets containing 1–25 mg of compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 58B Tablets containing 26–100 mg of compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 59 Parenteral injection

|  | Amount mg |
| --- | --- |
| Compound of formula (I) | 1 to 100 mg |
| Citric Acid Monohydrate | 0.75 mg |
| Sodium Phosphate | 4.5 mg |
| Sodium Chloride | 9 mg |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 60 Topical formulation

|  | Amount mg |
| --- | --- |
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

SUBSTANCE P ANTAGONISM ASSAY

A. Receptor Expression in Monkey Kidney Cell Line (COS)

To express the cloned human neurokinin-1-receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+ (trademark, STRATAGENE, La Jolla, Calif., USA)) into the Sac II site. Transfection of 20 ug of the plasmid DNA into 10 million COS cells was achieved by electroporation in 800 µl of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM N-2-hydroxyethyl-piperazine-N'- 2-ethane sulphonic acid (HEPES) pH 7.4) at 260 V and 950 µF using the IBI GENEZAPPER (trademark IBI, New Haven, Conn., USA). The cells were incubated in 10% fetal calf serum, 2 mM glutamine, 100 U/ml penicillin-streptomycin, and 90% DMEM media (GIBCO, Grand Island, N.Y., USA) in 5% $CO_2$ at 37° C. for three days before the binding assay.

B. Stable Expression in Chinese Hamster Ovarian Cell Line (CHO)

To establish a stable cell line expressing cloned human NK1R, the cDNA was subcloned into the vector pRcCMV (INVITROGEN). Transfection of 20 µg of the plasmid DNA into CHO cells was achieved by electroporation in 800 µl of transfection buffer supplemented with 0.625 mg/ml Herring sperm DNA at 300 V and 950 µF using the IBI GENEZA-PPER (IBI). The transfected cells were incubated in CHO media [10% fetal calf serum, 100 U/ml penicillin-streptomycin, 2 mM glutamine, 1/500 hypoxanthine-thymidine (ATCC), 90% IMDM media (JRH BIOSCIENCES, Lenexa, Kans., USA), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}I$-substance P ($^{125}I$-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavellette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 µl of the cell suspension would give rise to about 10,000 cpm of specific $^{125}I$-SP binding (approximately 50,000 to 200,000 cells). In the binding assay, 200 µl of cells were added to a tube containing 20 µl of 1.5 to 2.5 nM of $^{125}I$-SP and 20 µl of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 50 mM NaCl) three times and its radioactivity was determined by gamma counter.

The activation of phospholiphase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 5 µCi of $^3H$-myoinositol in 1 ml of media per well by overnight incubation. The extracellular radioactivity is removed by washing with phosphate buffered saline. LiCl is added to the well at final concentration of 10 mM with or without the test compound, and incubation is continued at 37° C. for 15 min. Substance P is added to the well at final concentration of 0.3 nM to activate the human NK1R. After 30 min of incubation at 37° C., the medium is removed and 0.1N HCl is added. Each well is sonicated at 4° C. and extracted with $CHCl_3$/methanol (1:1). The aqueous phase is applied to a 1 ml Dowex AG 1×8 ion exchange column. The column is washed with 0.1N formic acid followed by 0.025 M ammonium formate-0.1N formic acid. The inositol monophosphate is eluted with 0.2M ammonium formate-0.1N formic acid and quantitated by beta counter.

The data in Table 1 were obtained for compounds of formula (I):

TABLE 1

| SUBSTANCE P ANTAGONISM RESULTS | |
|---|---|
| Compound of Ex # | $IC_{50}$ @ NK1R (nM) |
| 1 | 14 |
| 2 | <3 |
| 4 | 2, 1.4 |
| 5 | 1 |
| 6 | 5, 6 |
| 7 | 3, 1.5 |
| 8 | 3 |
| 9 | 1 |
| 10 | 20 |
| 11 | 350 |
| 12 | 46% @ 1 µM |
| 13 | 300 |
| 14 | 100 |
| 15 | 60 |
| 16 | 80 |
| 17 | 200 |
| 18 | 0.6 |
| 19 | 0.9 |
| 20 | 2 |
| 21 | 40 |
| 22 | 5 |
| 23 | 35 |
| 24 | 15 |
| 25 | 70 |
| 26 | 41% @ 300 nM |
| 27 | 160 |
| 28 | 15 |
| 29 | 40 |
| 30 | 10 |
| 31 | 100 |
| 32 | 9 |
| 33 | >300 |
| 34 | 53% @ 1 µM |
| 35 | 100 |
| 36 | 0.5 |
| 37 | 150 |
| 38 | 150 |
| 39 | 0.9 |
| 40 | 15 |
| 41 | 100 |
| 42 | 45% @ 300 nM |
| 43 | 1.4 |
| 44 | 0.3 |
| 45 | 42% @ 300 nM |
| 47 | 2 |
| 48 | 45 |
| 49 | 20 |
| 50 | 2 |
| 51 | 40% @ 1 µM |
| 52 | 50 |
| 53 | 40% @ 300 nM |
| 55 | 2 |
| 56 | 25 |
| 57 | 2.5 |

We claim:

1. A compound of formula (I), or a salt or prodrug thereof:

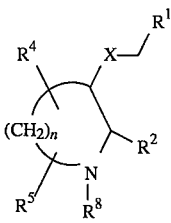

wherein
- n is 2 or 3 and any carbon atom of $(CH_2)_n$ may be substituted by $R^4$ and/or $R^5$;
- X represents O or S;
- $R^1$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, $-OR^a$, $SR^a$, $SOR^a$, $SO_2R^a$, $-NR^aR^b$, $-NR^aCOR^b$, $-NR^aCO_2R^b$, $-CO_2R^a$ or $-CONR^aR^b$;
- $R^2$ represents aryl selected from phenyl and naphthyl; heteroaryl selected from indazolyl, thienyl, furyl, pyridyl, thiazolyl, tetrazolyl and quinolyl; benzhydryl; or benzyl; wherein each aryl or heteroaryl moiety may be substituted by $C_{1-6}$alkyl, $C_{1-6}$alkoxy, halo or trifluoromethyl;
- $R^4$ and $R^5$ each independently represent H, halo, $CH_2OR^9$, $C_{1-6}$alkyl, oxo, $CO_2R^{10}$ or $CONR^{10}R^{11}$;
- $R^8$ represents H, $COR^9$, $CO_2R^{10}$, $COCONR^{10}R^{11}$, $COCO_2R^{10}$ or $C_{1-6}$alkyl optionally substituted by a group selected from ($CO_2R^{10}$, $CONR^{10}R^{11}$, hydroxy, cyano, $COR^9$, $NR^{10}R^{11}$, $C(NOH)NR^{10}R^{11}$, CONHphenyl($C_{1-4}$alkyl), $COCO_2R^{10}$, $COCONR^{10}R^{11}$ and phenyl optionally substituted by one or more substituents selected from $C_{1-6}$alkyl, $C_{1-6}$alkoxy, halo and trifluoromethyl);
- $R^a$ and $R^b$ each independently represent H, $C_{1-6}$alkyl, phenyl or trifluoromethyl;
- $R^9$ represents H, $C_{1-6}$alkyl or phenyl; and
- $R^{10}$ and $R^{11}$ each independently represent H or $C_{1-6}$alkyl.

2. A compound as claimed in claim 1 wherein n is 2 or 3; $R^4$ and $R^5$ each independently represent H, halo, $C_{1-6}$alkyl, $CO_2R^{10}$ or $CONR^{10}R^{11}$; and $R^8$ represents H, $COR^9$ or $C_{1-6}$alkyl optionally substituted by a group selected from ($CO_2R^{10}$, $CONR^{10}R^{11}$ and phenyl optionally substituted by $C_{1-6}$alkyl, $C_{1-6}$alkoxy, halo or trifluoromethyl).

3. A compound as claimed in claim 2 wherein $R^2$ represents phenyl or benzhydryl wherein any of the phenyl rings of the phenyl or benzhydryl moieties may optionally be substituted by halo or trifluoromethyl; $R^4$ and $R^5$ each independently represent H, $C_{1-6}$alkyl or $CO_2(C_{1-6}$alkyl); and $R^8$ represents H or $C_{1-6}$alkyl.

4. A compound as claimed in claim 1 wherein $R^1$ represents phenyl substituted by one or more substituents selected from $C_{1-6}$alkyl, nitro, trifluoromethyl, COOH, trimethylsilyl, bromo, chloro, iodo, cyano, $C_{1-6}$alkoxy and amino; $R^2$ represents unsubstituted or substituted phenyl, thienyl, pyridyl or benzhydryl; $R^4$ and $R^5$ each independently represent H, $C_{1-6}$alkyl, hydroxymethyl or oxo; and $R^8$ represents H, $COR^9$, $CO_2R^{10}$, $COCONR^{10}R^{11}$, $COCO_2R^{10}$, $C_{1-6}$alkyl or $C_{1-6}$alkyl substituted by $CO_2R^{10}$, $CONR^{10}R^{11}$, cyano, $C(NOH)NR^{10}R^{11}$, CONHphenyl($C_{1-4}$alkyl), or optionally substituted phenyl.

5. A compound as claimed in claim 1 wherein $R^8$ represents $C_{1-6}$alkyl substituted by $CO_2R^{10}$ or $CONR^{10}R^{11}$.

6. A compound as claimed in claim 1 wherein n is 3.

7. A compound as claimed in claim 1 wherein $R^2$ is unsubstituted phenyl.

8. A compound which is selected from:
cis-2-(diphenylmethyl)-3-(3,5-dimethylbenzyloxy)-1-methylpyrrolidine;
cis-3-((3,5-dimethylphenyl)methyloxy)-2-phenylpiperidine;
cis-3-((3,5-dimethylphenyl)methyloxy)-1-methyl-2-phenylpiperidine;
cis-3-((3,5-bis(trifluoromethyl)phenyl)methyloxy)-2-phenylpiperidine;
(+)-cis-3-((3,5-bis(trifluoromethyl)phenyl)methyloxy)-2-phenylpiperidine;
cis-3-((3,5-bis(trifluoromethyl)phenyl)methyloxy)- 1-(carbomethoxy)methyl-2-phenylpiperidine;
cis-3- ((3,5-bis(trifluoromethyl)phenyl)methyloxy)-1-(carboxamido)methyl-2-phenylpiperidine;
(+)-cis-3-((3,5-bis(trifluoromethyl)phenyl)methyloxy)-1-(carbomethoxy)methyl-2-phenylpiperidine;
(+)-cis-3-((3,5-bis(trifluoromethyl)phenyl)methyloxy)-1-(carboxamido)methyl-2-phenylpiperidine;
(+)-cis-3-((3,5-bis(trifluoromethyl)phenyl)methyloxy)-1-methyl-2-phenylpiperidine;
(−)-cis-3-((3,5-bis(trifluoromethyl)phenyl)methyloxy)-2-phenylpiperidine;
trans-3-((3,5-dimethylphenyl)methyloxy)-2-phenylpiperidine;
trans-3-((3,5-bis(trifluoromethyl)phenyl)methyloxy)-2-phenylpiperidine;
(2S,3S)-3-((3,5-bis(trifluoromethyl)phenyl)methyloxy)-1,1-dimethyl-2-phenylpiperidine;
(2S,3S)-1-acetyl-3-((3,5-bis(trifluoromethyl)phenyl)methyloxy)-2-phenylpiperidine;
(2S,3S)-1-formyl-3-((3,5-bis(trifluoromethyl)phenyl)methyloxy)-2-phenylpiperidine;
(2S,3S)-1-benzyl-3-((3,5-bis(trifluoromethyl)phenyl)methyloxy)-2-phenylpiperidine;
(2S,3S)-3-((3,5-bis(trifluoromethyl)phenyl)methyloxy)-1-(1-carbomethoxy)ethyl-2-phenylpiperidine;
(2S,3S)-3-((3,5-bis(trifluoromethyl)phenyl)methyloxy)-1(1-carboxamido)ethyl-2-phenylpiperidine;
cis-3-((3,5-bis(trifluoromethyl)phenyl)methyloxy)-6-methyl-2-phenylpiperidine;
cis-3-((3,5-bis(trifluoromethyl)phenyl)methyloxy)-2-(2-chlorophenyl)piperidine;
cis-3-((3,5-bis(trifluoromethyl)phenyl)methyloxy)-2-(3-chlorophenyl)piperidine;
cis-3-((3,5-bis(trifluoromethyl)phenyl)methyloxy)-2-(4-chlorophenyl)piperidine;
cis-3-((3,5-bis(trifluoromethyl)phenyl)methyloxy)-2-(4-methylphenyl)piperidine;
cis-3-((3,5-bis(trifluoromethyl)phenyl)methyloxy)-2-thienylpiperidine;
cis-3-((3,5-bis(trifluoromethyl)phenyl)methyloxy)-2-pyridylpiperidine;
cis-3-((3,5-bis(trifluoromethyl)phenyl)methyloxy)-6-keto-1-(4-methoxybenzyl)-2-phenylpiperidine;
cis-3-((3,5-bis(trifluoromethyl)phenyl)methyloxy)-6-keto-2-phenylpiperidine;
cis-3-((3,5-bis(trifluoromethyl)phenyl)methyloxy)-1-(2-carbomethoxy)ethyl- 2-phenylpiperidine;
cis-3-((3,5-bis(trifluoromethyl)phenyl)methyloxy)-1-(carboxamido)ethyl- 2-phenylpiperidine;
cis-3-((3,5-bis(trifluoromethyl)phenyl)methyloxy)-1-(3-carbomethoxy)propyl- 2-phenylpiperidine;
cis-3-((3,5-bis(trifluoromethyl)phenyl)methyloxy)-1-(3-carboxamido)propyl- 2-phenylpiperidine;
(2S,3S)-1-t-butoxycarbonyl-3-((3-methyl-5-(trimethylsilyl)phenyl)methoxy- 2-phenylpiperidine;

cis-2-phenyl-3-(phenylmethyloxy)piperidine;
cis-3-((3,5-di-t-butylphenyl)methyloxy)-2-phenylpiperidine;
(2S,3S)-3-(((3-methyl-5-iodo)phenyl)methyloxy)-2-phenylpiperidine;
cis-3-((3,5-bis(trifluoromethyl)phenyl)methyloxy)-1-carbomethoxyformyl- 2-phenylpiperidine;
cis-3-((3,5-bis(trifluoromethyl)phenyl)methyloxy)-1-carboxamidoformyl- 2-phenylpiperidine;
cis-N-(1-acetamidooxime)3-((3,5-bis(trifluoromethyl) phenyl)methyloxy)-2-phenylpiperidine;
cis-3-((3,5-bis(trifluoromethyl)phenyl)methyloxy)-1-cyanomethyl- 2-phenylpiperidine;
(+)-cis-3-((3,5-bis(trifluoromethyl)phenyl)methyloxy)-1-carboxymethyl- 2-phenylpiperidine;
cis-3-((3,5-bis(trifluoromethyl)phenyl)methyloxy)-1-(( 3,5-bis(trifluoromethyl)phenyl)methyl)-2-phenylpiperidine;
cis-3-((3,5-bis(trifluoromethyl)phenyl)methyloxy)-1-(N,N-diethylcarboxamido)methyl- 2-phenylpiperidine;
cis-3-((3-methyl-5-trimethylsilyl-benzyloxy)-2-phenylpiperidine;
cis-3-((2-methoxy-5-nitrophenyl)methyloxy)-2-phenylpiperidine;
cis-3-((2-methoxy-5-aminophenyl)methyloxy)-2-phenylpiperidine;
cis-3-((3,5-dichlorophenyl)methyloxy)-2-phenylpiperidine;
3-((3,5-bis(trifluoromethyl)phenyl)methyloxy)-3-methyl-2-phenylpiperidine;
3-((3,5-bis(trifluoromethyl)phenyl)methyloxy)-2-methyl-2-phenylpiperidine;
cis-3-((3,5-bis(trifluoromethyl)phenyl)methyloxy)-1-(N-benzylcarboxamido)methyl- 2-phenylpiperidine;
cis-3-((3,5-bis(trifluoromethyl)phenyl)methyloxy)-1-(N-methylcarboxamido)methyl- 2-phenylpiperidine;
cis-3-((3-bromophenyl)methyloxy)-2-phenylpiperidine;
cis-3-((3-cyanophenyl)methyloxy)-2-phenylpiperidine;
cis-3-((3-carboxyphenyl)methyloxy)-2-phenylpiperidine;
cis-3-((3,5-bis(trifluoromethyl)phenyl)methyloxy)-6-hydroxymethyl- 2-phenylpiperidine;
(2S,3S)-3-((3,5-bis(trifluoromethyl)phenyl)methyloxy)-1-(N-t-butylcarboxamidomethyl)- 2-phenylpiperidine;
(2S,3S)-3-((3,5-bis(trifluoromethyl)phenyl)methyloxy)-1-((N-cyclopropyl)carboxamidomethyl)- 2-phenylpiperidine; and salts and prodrugs thereof.

9. A pharmaceutical composition comprising a compound as claimed in any of claims 1 to 8 in association with a pharmaceutically acceptable carrier.

10. A process for the preparation of a compound as claimed in claim 1, which process comprises reacting a compound of formula (III) with a compound of formula (IV):

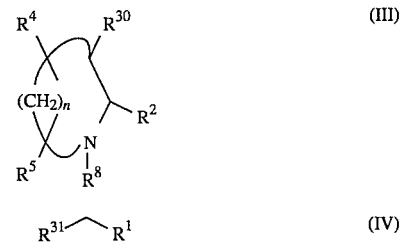

wherein $R^1$, $R^2$, $R^4$, $R^5$ and n are as defined for formula (I), $R^8$ is as defined for formula (I) except that, when $R^8$ is H it is replaced by a suitable protecting group, such as $CO_2(C_{1-6}alkyl)$; and one of $R^{30}$ and $R^{31}$ represents a leaving group and the other of $R^{30}$ and $R^{31}$ represents XH, where X is as defined for formula (I); in the presence of a base, followed by deprotection, if required; and optionally converting the compound of formula (I) so prepared to another compound of formula (I), or a salt or prodrug thereof.

11. A method for the treatment or prevention of a physiological disorder associated with an excess of tachykinins, which method comprises administration to a patient in need thereof of a tachykinin-reducing amount of a compound according to claim 1.

12. A method according to claim 11 for the treatment or prevention of pain or inflammation.

13. A method according to claim 11 for the treatment or prevention of migraine.

14. A method according to claim 11 for the treatment or prevention of postherpetic neuralgia.

* * * * *